(12) United States Patent
Frey et al.

(10) Patent No.: US 7,914,655 B2
(45) Date of Patent: *Mar. 29, 2011

(54) POTENTIOSTATIC CIRCUIT ARRANGEMENT ON A BIOSENSOR FOR DIGITISATION OF THE MEASURED CURRENT

(75) Inventors: Alexander Frey, Taufkirchen (DE); Christian Paulus, Weilheim (DE); Meinrad Schienle, Ottobrunn (DE); Roland Thewes, Gröbenzell (DE)

(73) Assignee: Siemens Aktiengesellschaft, Munich (DE)

( * ) Notice: Subject to any disclaimer, the term of this patent is extended or adjusted under 35 U.S.C. 154(b) by 1250 days.

This patent is subject to a terminal disclaimer.

(21) Appl. No.: 10/556,731

(22) PCT Filed: May 11, 2004

(86) PCT No.: PCT/DE2004/000977
§ 371 (c)(1),
(2), (4) Date: Aug. 23, 2006

(87) PCT Pub. No.: WO2004/102211
PCT Pub. Date: Nov. 25, 2004

(65) Prior Publication Data
US 2007/0080060 A1     Apr. 12, 2007

(30) Foreign Application Priority Data

May 13, 2003 (DE) .................................. 103 21 490

(51) Int. Cl.
*G01N 27/327* (2006.01)
*G01R 19/12* (2006.01)

(52) U.S. Cl. ..................... 204/406; 204/403.01; 324/686
(58) Field of Classification Search ............. 204/403.01, 204/406; 324/686
See application file for complete search history.

(56) References Cited

U.S. PATENT DOCUMENTS 5,217,595 A * 6/1993 Smith et al. ................... 204/412
6,277,255 B1 * 8/2001 Green et al. .................. 204/406

(Continued)

FOREIGN PATENT DOCUMENTS

WO     WO 02/33397 A1    4/2002

OTHER PUBLICATIONS

Bard and Faulkner, Electrochemical Methods: Fundamentals and Applications, 2nd ed, 2001, pp. 643 and 644.*

(Continued)

*Primary Examiner* — Kaj K Olsen
(74) *Attorney, Agent, or Firm* — Harness, Dickey & Pierce, P.L.C.

(57) ABSTRACT

A circuit arrangement, an electrochemical sensor, a sensor arrangement, and a method for processing a current signal provided by a sensor electrode are disclosed. The circuit arrangement includes a sensor electrode, a first circuit unit, electrically coupled to the sensor electrode and a second circuit unit, including a first capacitor, whereby the first circuit arrangement is embodied to hold the electrical potential of the sensor electrode in a given first reference range about a set electrical potential and, when the sensor electrode potential falls outside the first reference range, the first capacitor and the sensor electrode are coupled such that a matching of the electrical potentials is possible. The second circuit unit is embodied such that, when the electrical potential of the first capacitor falls outside a second reference range, this event is detected and the first capacitor brought to a first electrical reference potential.

7 Claims, 15 Drawing Sheets

U.S. PATENT DOCUMENTS 6,294,062 B1 * 9/2001 Buck et al. .................. 204/400
7,123,029 B2 * 10/2006 Frey et al. .................. 324/686
2003/0094383 A1 * 5/2003 Kermani .................. 205/777.5

OTHER PUBLICATIONS

Thewes R. et al: "Sensor arrays for fully-electronic DNA detection on CMOS", ISSCC2002, Bd. 1, 2002, S. 350-351, 472, XP010585601, S. 350, rechte Spalte, Abs. 3: Abb. 21.2.5.

Hofmann F. et al: "Passive DNA Sensor with Gold Electrodes Fabricated in a CMOS Backend Process", Proceedings of the European Solid State Device Research Conference (ESSDERC), Edition Frontieres, GIL-SUR-YVETTE, FR, Sep. 24, 2002, S. 487-490, XP008033777, Abb. 2,4.

Uster M. et al: "Integrating ADC using a Single Transistor as Integrator and Amplifier for very low (1 FA Minimum) input currents", Int. Converence on Advanced A/D and D/A Conversion Techniques and their Applications, XX, XX, Jul. 27, 1999, S. 86-89, XP001147236, in der Anmeldung erwähnt, Abb. 1, 2.

Breten M. at al: "Integrating data converters for Picoampere currents from electrochemical transducer", ISCAS 2000, Bd. 5, May 28, 2000, S. 709-712, XP010504295, Abb. 1.

Hintsche, R. et al. "Microbiosensors using electrodes made in Si-technology", Frontiers in Biosensorics. Fundamental Aspects, Scheller, FW, Schubert F., Fredrowitz, J. (eds.), Birkhauser Verlag Basel, Schweiz, S. 267-283, 1997.

van Gerwen, P. (1997), "Nanoscaled Interdigitated Electrode Arrays for Biochemical Sensors", IEEE, Int. Conf. on Solid-State Sensors and Actuators, Jun. 16-19, 1997, Chicago, S.907-910.

Paeschke, M., Dietrich, F., Uhlig, A. Hintsche, R. (1996) "Voltammetric Multichannel Measurements Using Silicon Fabricated Microelectrode Arrays", Electroanalysis, vol. 7, No. 1, S.1-8.

* cited by examiner

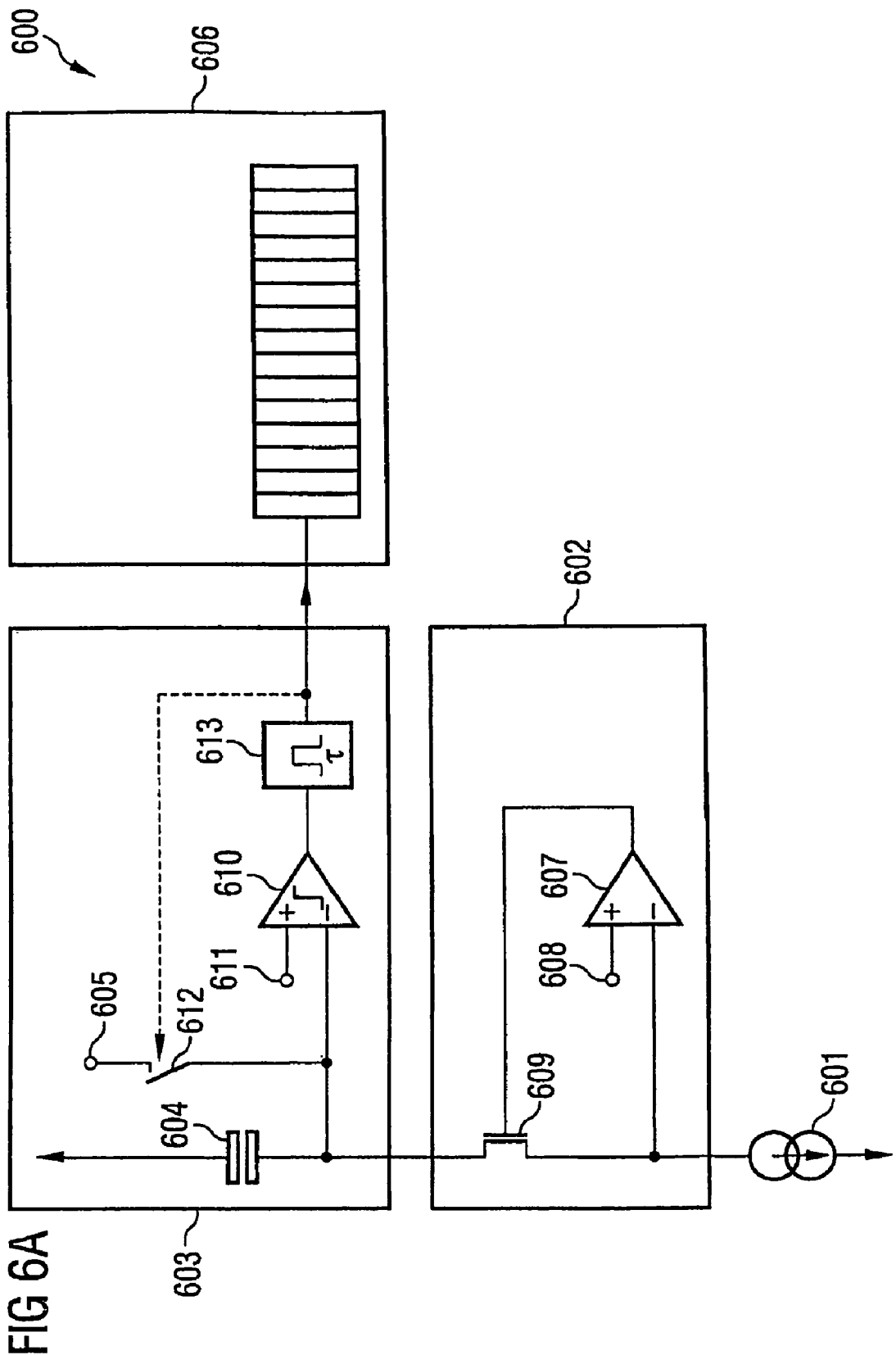

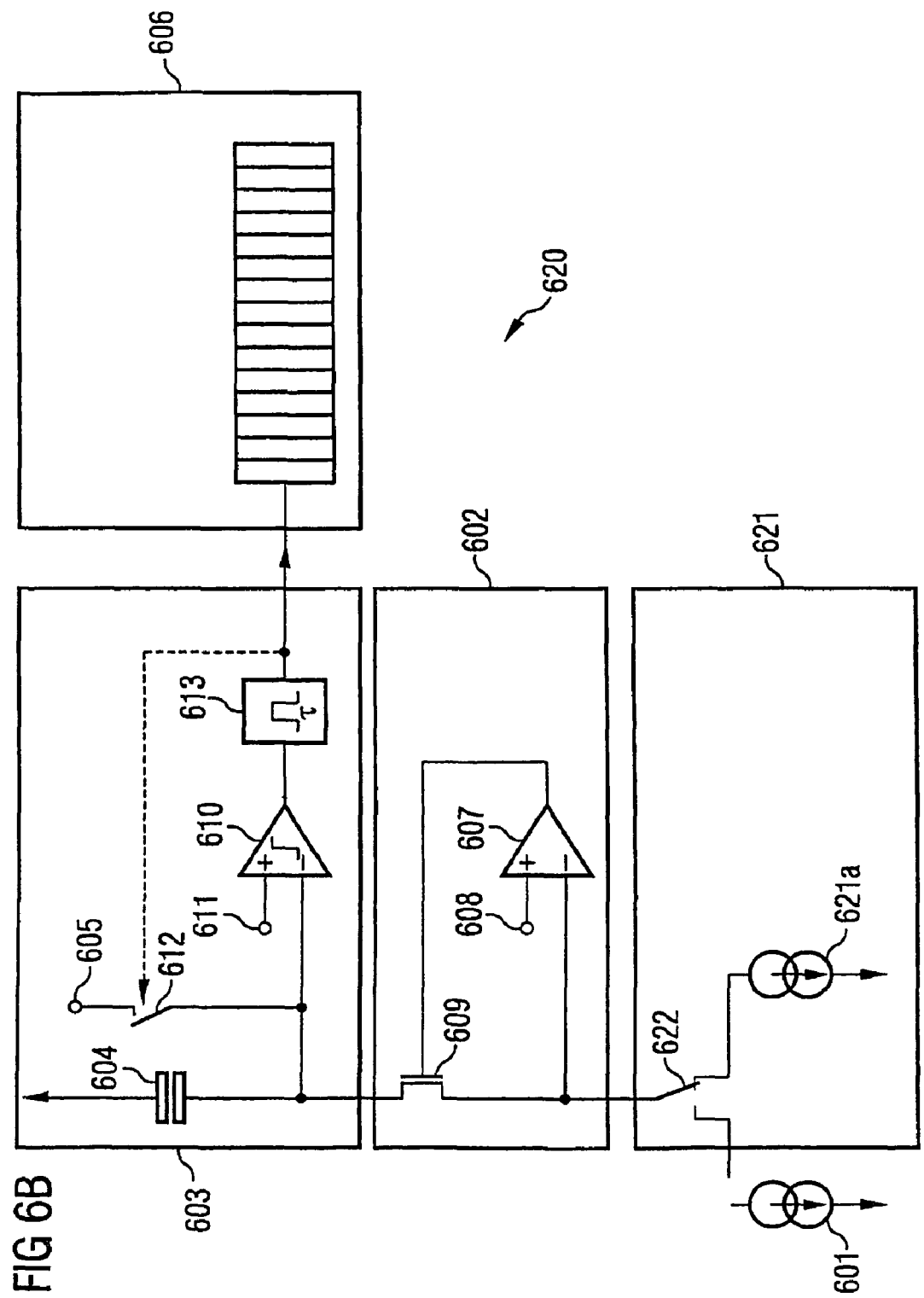

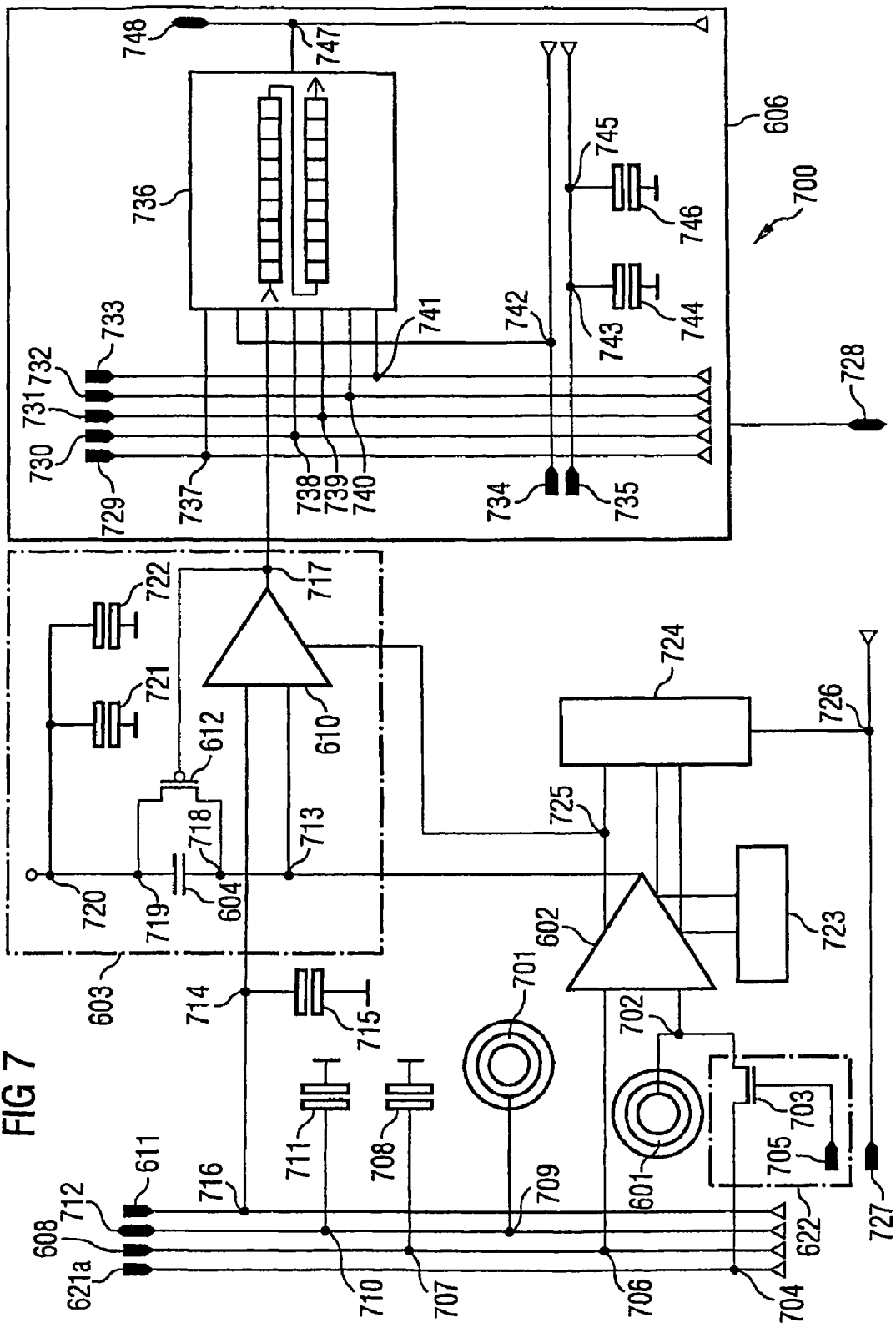

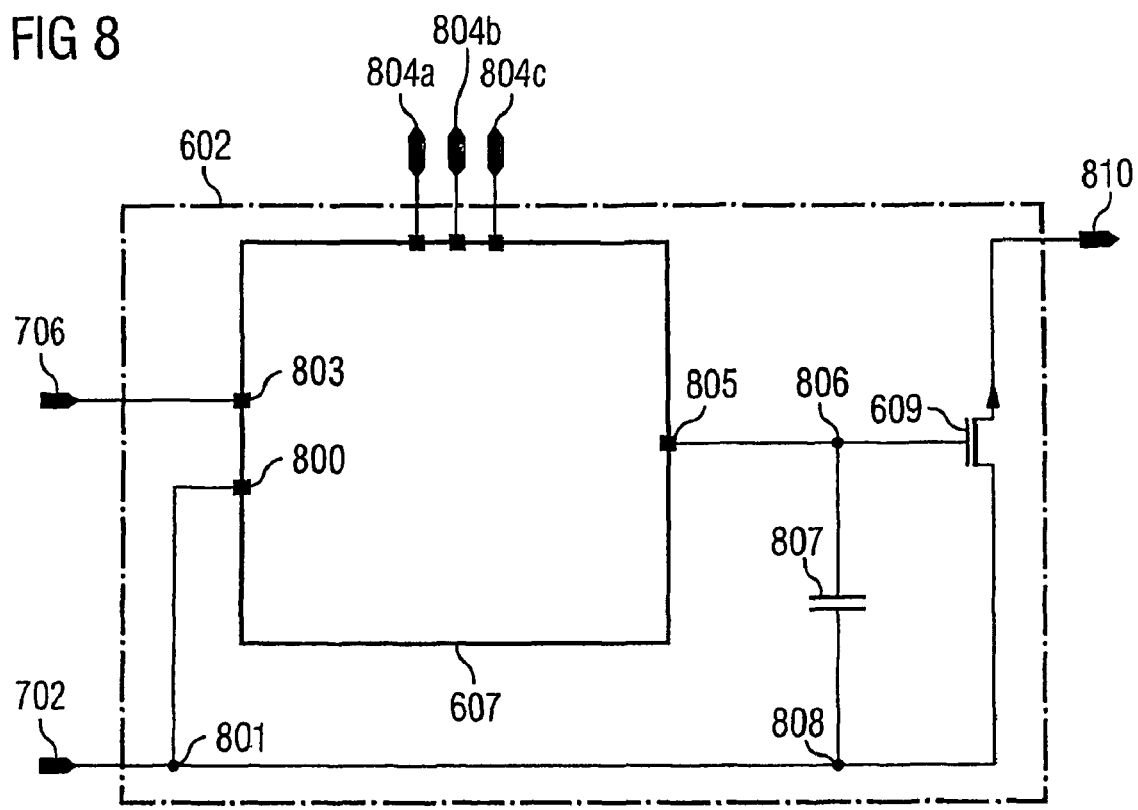

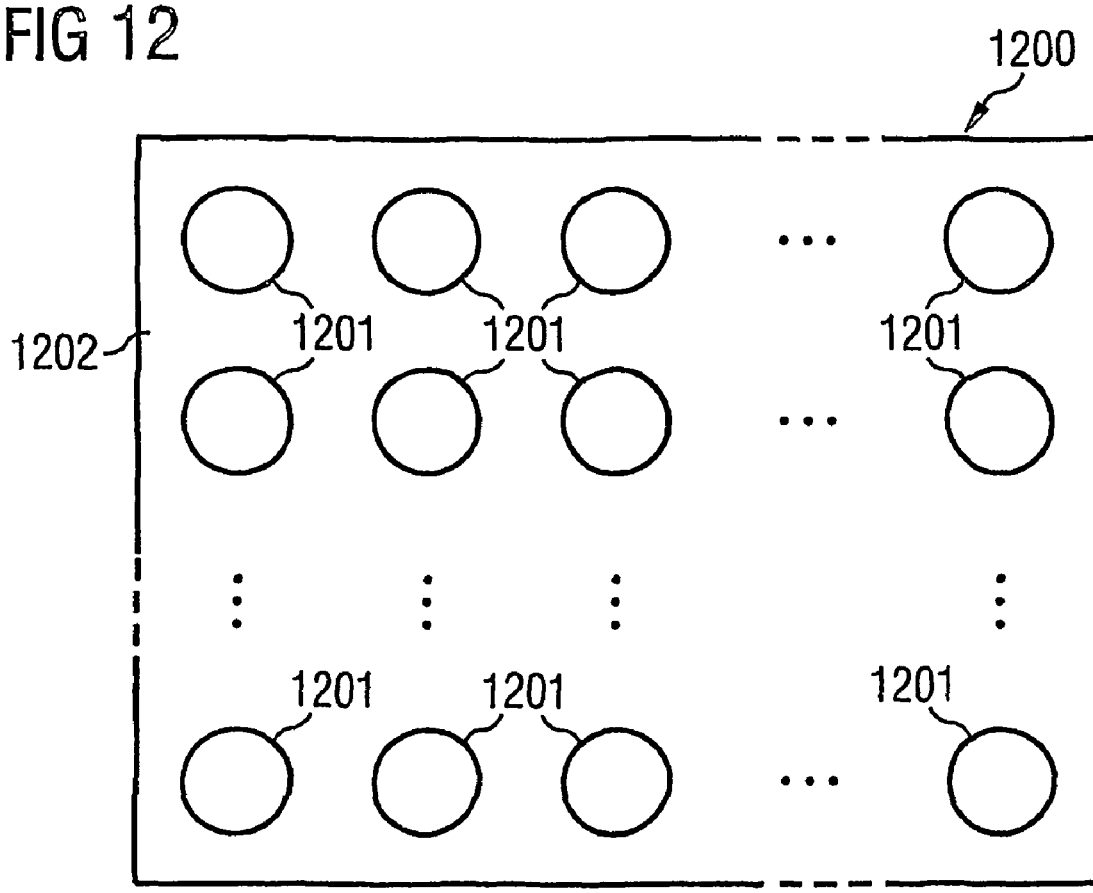

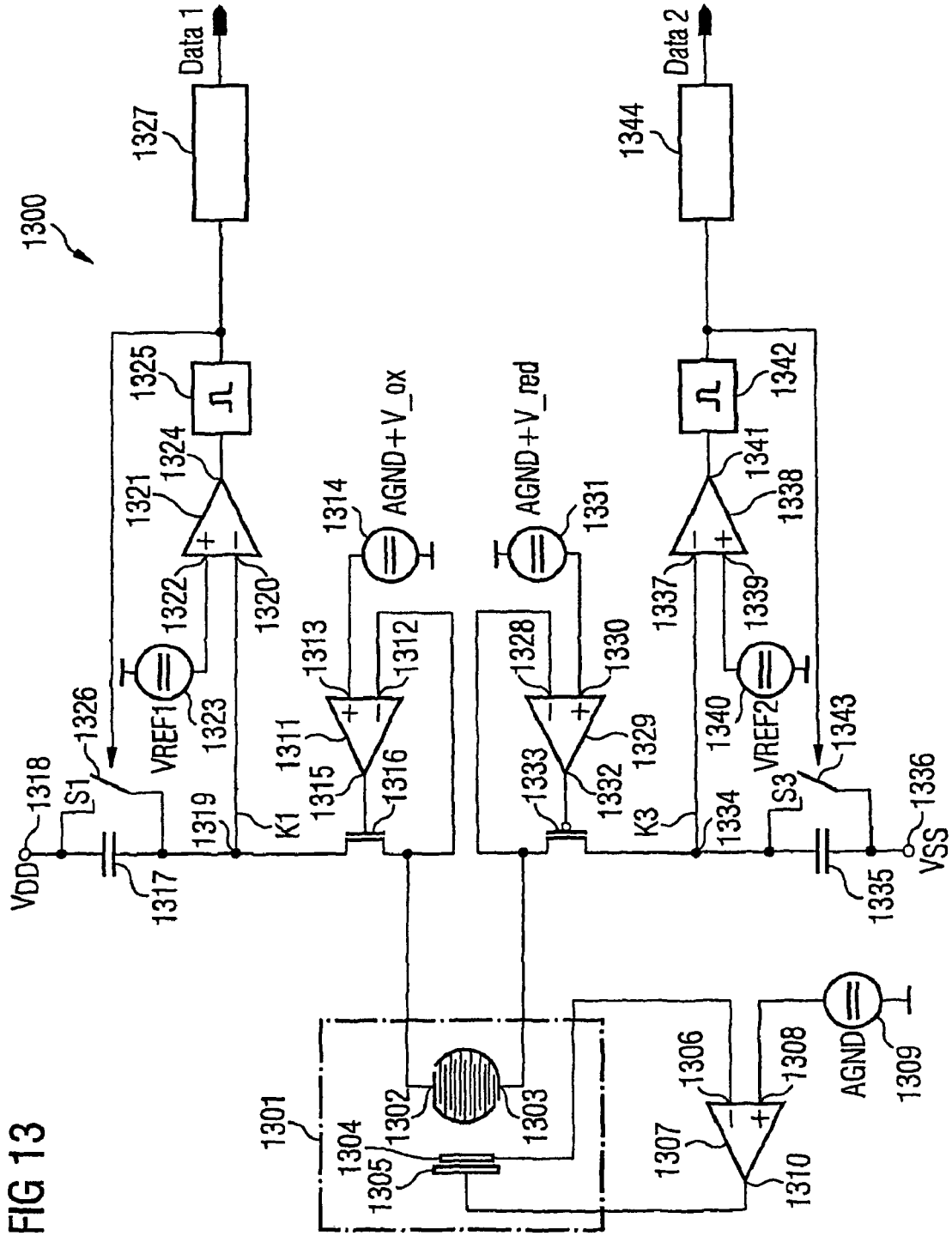

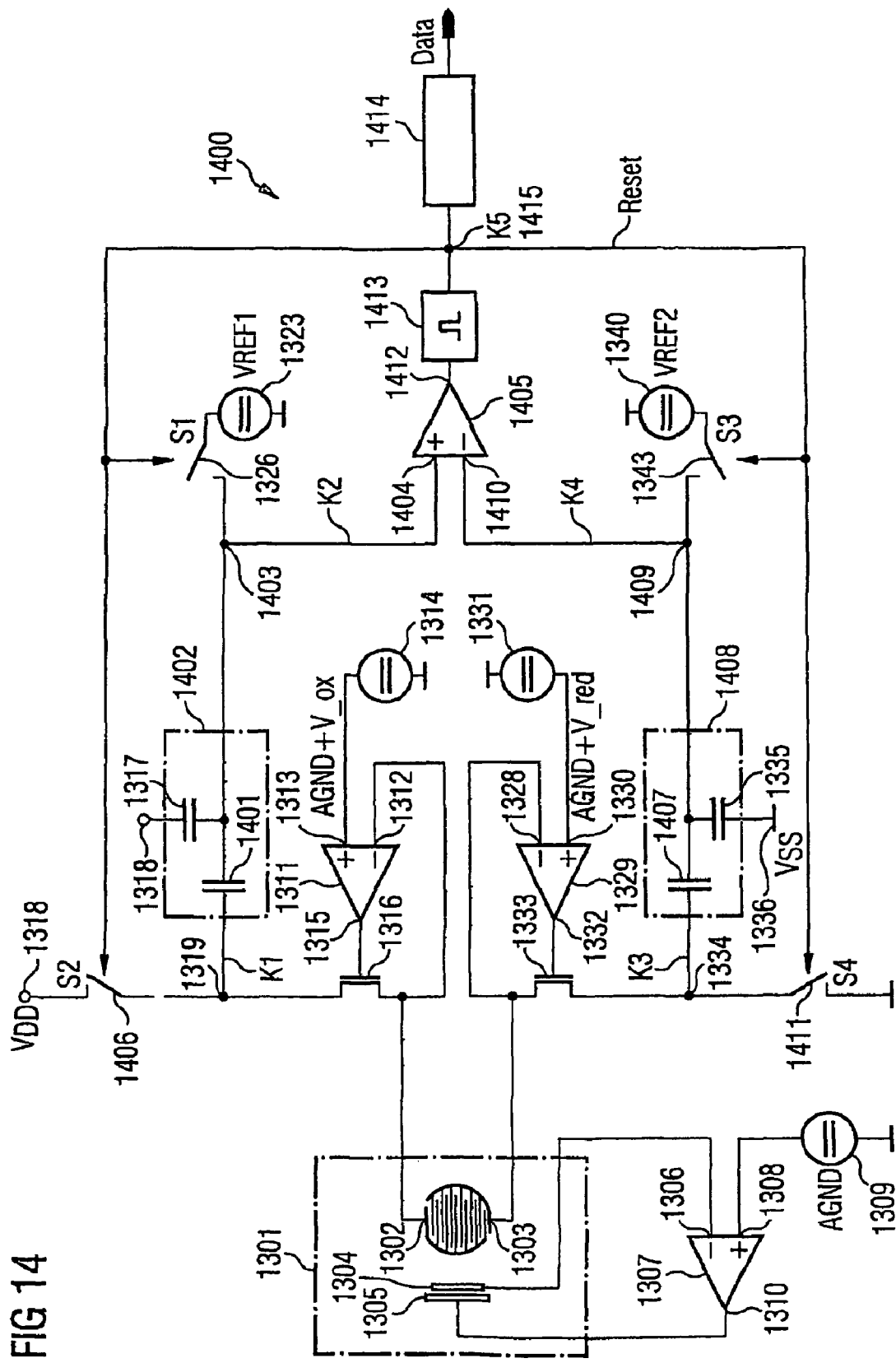

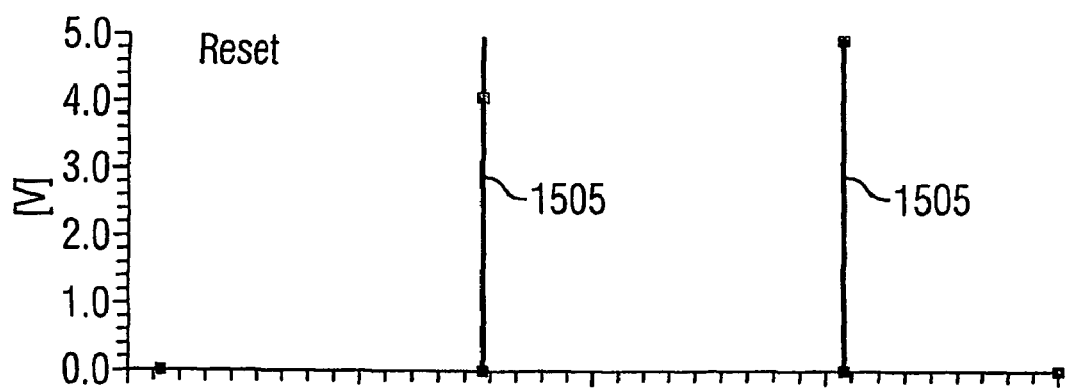
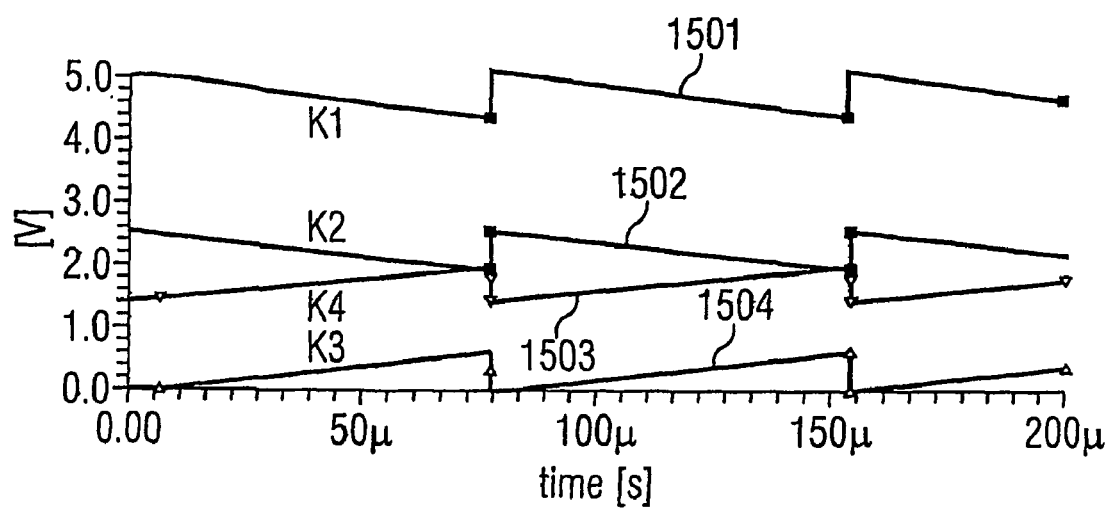

US 7,914,655 B2

POTENTIOSTATIC CIRCUIT ARRANGEMENT ON A BIOSENSOR FOR DIGITISATION OF THE MEASURED CURRENT

This application is the national phase under 35 U.S.C. §371 of PCT International Application No. PCT/DE2004/000977 which has an International filing date of May 11, 2004, which designated the United States of America and which claims priority on German Patent Application number DE 103 21 490.9 filed May 13, 2003, the entire contents of which are hereby incorporated herein by reference.

FIELD

The invention generally relates to a circuit arrangement, an electrochemical sensor, a sensor arrangement and/or a method for processing a current signal provided via a sensor electrode.

BACKGROUND

FIG. 2A and FIG. 2B show a biosensor chip, as described in [1]. The sensor 200 has two electrodes 201, 202 made of gold, which are embedded in an insulator layer 203 made of electrically insulating material. Connected to the electrodes 201, 202 are electrode terminals 204, 205, by which the electrical potential can be applied to the electrode 201, 202. The electrodes 201, 202 are configured as planar electrodes. DNA probe molecules 206 (also referred to as catcher molecules) are immobilized on each electrode 201, 203 (cf. FIG. 2A). The immobilization is effected in accordance with the gold-sulfur coupling. The analyte to be investigated, for example an electrolyte 207, is applied on the electrodes 201, 202.

If the electrolyte 207 contains DNA strands 208 with a base sequence which is complementary to the sequence of the DNA probe molecules 206, i.e. which sterically match the catcher molecules in accordance with the key/lock principle, then these DNA strands 208 hybridize with the DNA probe molecules 206 (cf. FIG. 2B).

Hybridization of a DNA probe molecule 206 and a DNA strand 208 takes place only when the sequences of the respective DNA probe molecule and of the corresponding DNA strand 208 are complementary to one another. If this is not the case, then no hybridization takes place. Thus, a DNA probe molecule having a predetermined sequence is in each case only capable of binding a specific DNA strand, namely the one with a respectively complementary sequence, that is to say of hybridizing with it, which results in the high degree of selectivity of the sensor 200.

If hybridization takes place, then the value of the impedance between the electrodes 201 and 202 changes, as can be seen from FIG. 2B. This changed impedance is detected by applying a suitable electrical voltage to the electrode terminals 204, 205 and by registering the current resulting from this.

In the case of hybridization, the impedance between the electrodes 201, 202 changes. This can be attributed to the fact that both the DNA probe molecules 206 and the DNA strands 208, which possibly hybridize with the DNA probe molecules 206, have poorer electrical conductivity than the electrolyte 207 and thus, as can be seen, in part electrically shield the respective electrode 201, 202.

In order to improve the measurement accuracy, it is known from [2] to use a plurality of electrode pairs 201, 202 and to arrange the latter in parallel with one another, these being arranged intermeshed with one another, as can be seen, so that the result is a so-called interdigital electrode 300, FIG. 3A showing the plan view thereof and FIG. 3B showing the cross-sectional view thereof along the section line I-I' from FIG. 3A.

Furthermore, principles relating to a reduction/oxidation recycling process for registering macromolecular biomolecules are known for example from [1], [3]. The reduction/oxidation recycling process, also referred to hereinafter as the redox cycling process, will be explained in more detail below with reference to FIG. 4A, FIG. 4B, FIG. 4C.

FIG. 4A shows a biosensor 400 having a first electrode 401 and a second electrode 402, which are applied on an insulator layer 403. A holding region 404 is applied on the first electrode 401 made of gold. The holding region 404 serves for immobilizing the DNA probe molecules 405 on the first electrode 401. Such a holding region is not provided on the second electrode 402.

If DNA strands 407 having a sequence which is complementary to the sequence of the immobilized DNA probe molecules 405 are intended to be registered by use of the biosensor 400, then the sensor 400 is brought into contact with a solution to be investigated, for example an electrolyte 406, in such a way that DNA strands 407 possibly contained in the solution 406 to be investigated can hybridize with the complementary sequence to the sequence of the DNA probe molecules 405.

FIG. 4B shows the case where the DNA strands 407 to be registered are contained in the solution 406 to be investigated and have hybridized with the DNA probe molecules 405.

The DNA strands 407 in the solution to be investigated are marked with an enzyme 408, with which it is possible to cleave molecules described below into partial molecules, at least one of which is redox-active. It is customary to provide a considerably larger number of DNA probe molecules 405 than there are DNA strands 407 to be determined contained in the solution 406 to be investigated.

After the DNA strands 407 possibly contained in the solution 406 to be investigated together with the enzyme 408 are hybridized with the immobilized DNA probe molecules 405, the biosensor 400 is rinsed, as a result of which the nonhybridized DNA strands are removed and the biosensor chip 400 is cleaned of the solution 406 to be investigated. The rinsing solution used for rinsing or a further solution supplied separately in a further phase has an electrically uncharged substance added to it, which contains molecules that can be cleaved by means of the enzyme 408 at the hybridized DNA strands 407, into a first partial molecule 410 and into a second partial molecule. One of the two molecules is redox-active.

As shown in FIG. 4C, the for example negatively charged first partial molecules 410 are attracted to the positively charged first electrode 401, which is indicated by the arrow 411 in FIG. 4C. The negatively charged first partial molecules 410 are oxidized at the first electrode 401, which has a positive electrical potential, and are attracted as oxidized partial molecules 413 to the negatively charged second electrode 402, where they are reduced again. The reduced partial molecules 414 again migrate to the positively charged first electrode 401. In this way, an electrical circulating current is generated, which is proportional to the number of charge carriers respectively generated by way of the enzymes 406.

The electrical parameter which is evaluated in this method is the change in the electric current $m=dI/dt$ as a function of the time t, as is illustrated schematically in the diagram 500 in FIG. 5.

FIG. 5 shows the function of the electric current 501 depending on the time 502. The resulting curve profile 503 has an offset current $I_{offset}$ 504, which is independent of the temporal profile. The offset current $I_{offset}$ 504 is generated on account of non-idealities of the biosensor 400. An essential cause of the offset current $I_{offset}$ resides in the fact that the covering of the first electrode 401 with the DNA probe molecules 405 is not effected in an ideal manner, i.e. not completely densely. In the case of a completely dense coverage of the first electrode 401 with the DNA probe molecules 405, an essentially capacitive electrical coupling would result on account of the so-called double-layer capacitance, which is produced by the immobilized DNA probe molecules 405, between the first electrode 401 and the electrically conductive solution 406 to be investigated. However, the incomplete coverage leads to parasitic current paths between the first electrode 401 and the solution 406 to be investigated, which inter alia also have resistive components.

However, in order to enable the oxidation/reduction process, the coverage of the first electrode 401 with the DNA probe molecules 405 is intended not to be complete at all, in order that the electrically charged partial molecules, i.e. the negatively charged first partial molecules 410, can pass to the first electrode 401 on account of an electrical force and also as a result of diffusion processes. In order, on the other hand, to achieve the greatest possible sensitivity of such a biosensor, and in order simultaneously to achieve the least possible parasitic effects, the coverage of the first electrode 401 with DNA probe molecules 405 should be sufficiently dense. In order to achieve a high reproducibility of the measured values determined by means of such a biosensor 400, both electrodes 401, 402 are intended always to provide an adequately large area afforded for the oxidation/reduction process in the context of the redox cycling process.

Macromolecular biomolecules are to be understood for example as proteins or peptides or else DNA strands having a respectively predetermined sequence. If proteins or peptides are intended to be registered as macromolecular biomolecules, then the first molecules and the second molecules are ligands, for example active substances with a possible binding activity, which bind the proteins or peptides to be registered to the respective electrode on which the corresponding ligands are arranged. Ligands that may be used are enzyme agonists, pharmaceuticals, sugars or antibodies or some other molecule which has the capability of specifically binding proteins or peptides.

If the macromolecular biomolecules used are DNA strands having a predetermined sequence which are intended to be registered by use of the biosensor, then it is possible, by means of the biosensor, for DNA strands having a predetermined sequence to be hybridized with DNA probe molecules having the sequence that is complementary to the sequence of the DNA strands as molecules on the first electrode.

A probe molecule (also called catcher molecule) is to be understood as a ligand or a DNA probe molecule.

The value m=dI/dt introduced above, which corresponds to the gradient of the straight line 503 from FIG. 5, depends on the length and also the width of the electrodes used for registering the measurement current. Therefore, the value m is approximately proportional to the longitudinal extent of the electrodes used, for example in the case of the first electrode 201 and the second electrode 202 proportional to the length thereof perpendicular to the plane of the drawing in FIG. 2A and FIG. 2B. If a plurality of electrodes are connected in parallel, for example in the known interdigital electrode arrangement (cf. FIG. 3A, FIG. 3B), then the change in the measurement current is proportional to the number of electrodes respectively connected in parallel.

However, the value of the change in the measurement current may have a range of values that fluctuates to a very great extent, on account of various influences, the current range that can be detected by a sensor being referred to as the dynamic range. A current intensity range of five decades is often mentioned as a desirable dynamic range. Causes of the great fluctuations may be, in addition to the sensor geometry, also biochemical boundary conditions. Thus, it is possible that macromolecular biomolecules of different types to be registered will bring about greatly different ranges of values for the resulting measurement signal, i.e. in particular the measurement current and the temporal change thereof, which in turn leads to a widening of the required overall dynamic range with corresponding requirements for a predetermined electrode configuration with downstream uniform measurement electronics.

The requirements made of the large dynamic range of such a circuit have the effect that the measurement electronics are expensive and complicated in their configuration, in order to operate sufficiently accurately and reliably in the required dynamic range.

Furthermore, the offset current $I_{offset}$ is often much greater than the temporal change in the measurement current m over the entire measurement duration. In such a scenario, it is necessary, within a large signal, to measure a very small time-dependent change with high accuracy. This makes very high requirements of the measurement instruments used, which makes the registering of the measurement current complex, complicated and expensive. This fact is also at odds with a miniaturization of sensor arrangements that is striven for.

To summarize, the requirements made of the dynamic range and therefore of the quality of a circuit for detecting sensor events are extremely high.

It is known, during circuit design, to take account of the non-idealities of the components used (noise, parameter variations) in the form such that an operating point at which these non-idealities play a part that is as negligible as possible is chosen for these components in the circuit.

If a circuit is intended to be operated over a large dynamic range, maintaining an optimum operating point over all the ranges becomes increasingly more difficult, more complex and thus more expensive, however.

Small signal currents that are obtained at a sensor, for example, can be raised, with the aid of amplifier circuits, to a level that permits the signal current to be forwarded for example to an external device or internal quantification.

A digital interface between the sensor and the evaluating system is advantageous for reasons of interference immunity and user-friendliness. Thus, the analog measurement currents are intended to be converted into digital signals actually in the vicinity of the sensor, which can be effected by an integrated analog-to-digital converter (ADC). Such an integrated concept for digitizing an analog, small current signal is described in [4], for example.

In order to achieve the required dynamic range, the ADC should have a correspondingly high resolution and a sufficiently high signal-to-noise ratio. Integrating such an analog-to-digital converter in direct proximity to a sensor electrode furthermore constitutes a high technological challenge, and the corresponding process implementation is complex and expensive. Furthermore, achieving a sufficiently high signal-to-noise ratio in the sensor is extremely difficult.

[5] discloses a current-mode analog/digital converter which is configured for a maximum input current range of 5 nA and a resolution of the order of magnitude of 1 pA.

[6] discloses a device for determining and characterizing the gradients of time-variable signals.

[7] discloses an electronic circuit for tracking an electronic signal for the purpose of determining whether the gradient of the signal at a predetermined time is greater than or equal to a predetermined value.

SUMMARY

At least one embodiment of the invention is based on the problem of providing an error-robust circuit arrangement with an improved detection sensitivity for electric currents that are very weakly variable with respect to time.

The problem is reduced or even solved by a circuit arrangement, an electrochemical sensor, a sensor arrangement and/or a method for processing a current signal provided via a sensor electrode.

At least one embodiment of the invention provides a circuit arrangement having a sensor electrode, having a first circuit unit, which is electrically coupled to the sensor electrode, and having a second circuit unit, which has a first capacitor. The first circuit unit is set up in such a way that it holds the electrical potential of the sensor electrode in a predeterminable first reference range around a predeterminable electrical desired potential by coupling the first capacitor and the sensor electrode in such a way that a matching of the electrical potential is made possible. The second circuit unit is set up in such a way that, if the electrical potential of the first capacitor is outside a second reference range, said second circuit unit detects this event and brings the first capacitor to a first electrical reference potential.

The functionality of the circuit arrangement according to at least one embodiment of the invention is explained clearly below. The circuit arrangement of at least one embodiment of the invention has a sensor electrode at which a sensor event may take place.

By way of example, a hybridization event between DNA half strands contained in a liquid to be investigated and capture molecules immobilized on the sensor electrode may be effected at the sensor electrode. If the molecules to be registered have an enzyme label, for example, which generates free electrical charge carriers in the liquid to be investigated, then an electric current signal to be detected flows proceeding from the sensor electrode into the circuit arrangement of at least one embodiment of the invention.

The first circuit unit of the circuit arrangement is set up in such a way that this clearly holds the electrical potential of the sensor electrode within a first reference range. As long as the electrical potential of the sensor electrode is within said reference range, the first circuit unit decouples the sensor electrode from a capacitor of the second circuit unit. If the electrical potential of the sensor electrode moves outside the first reference range, then the first circuit unit produces a gradual electrical coupling between the sensor electrode and the first capacitor of the second circuit unit.

A matching of the electrical potential of the sensor electrode to that of the first capacitor of the second circuit unit is made possible on account of the electrical coupling. Clearly, free electrical charges can flow back and forth between the capacitor and the sensor electrode, in such a way that the electrical potential of the sensor electrode is brought back into the first reference range. As a result, small quantities of charge can be progressively shifted proceeding from the sensor electrode onto the second capacitor of the second circuit unit, or vice versa.

Clearly, small sensor currents are integrated up to form a charge packet on the capacitor until the charge packet has a predetermined sufficient size to be detected. Therefore, the quantity of charge situated on the first capacitor of the second circuit unit changes in a manner characteristic of the number of sensor events effected on the sensor electrode.

In other words, the first capacitor of the second circuit unit subsequently supplies to the sensor electrode that quantity of charge which flows away from the sensor electrode on account of the sensor events. Therefore, the first circuit unit and the capacitor function inter alia in a manner similar to a potentiostat, by holding the electrical voltage of the sensor electrode within the first reference range, preferably at the electrical desired potential.

However, if the electrical potential of the first capacitor moves outside the second reference range on account of the charge carriers exchanged with the sensor electrode, then this event is detected by the second circuit unit, and the second circuit unit ensures that the first capacitor is brought to a first electrical reference potential. To put it clearly, the second circuit unit forms the following functionality: if a sufficiently large quantity of charge has been taken from the first capacitor by the sensor electrode (or conversely if a sufficiently large quantity of charge has flowed from the sensor electrode onto the first capacitor), this event is detected by the second circuit unit for example by outputting of a pulse. Furthermore, the electrical charge that has flowed away onto the sensor electrode is subsequently supplied to the first capacitor (or the electrical charge that has flowed from the sensor electrode onto the first capacitor is taken from the first capacitor) in order to return the capacitor again to a defined operating point, i.e. to the first electrical reference potential.

The circuit arrangement according to at least one embodiment of the invention having the functionality described is suitable for registering extremely small analog electric current signals and converting them into a digital signal, i.e. a sequence of temporally successive, separate pulses. The analog measurement signal is digitized in direct spatial proximity to the sensor electrode, thereby largely avoiding parasitic, additional noise on account of a temporally as well as spatially long communication path of an analog signal. Therefore, the circuit arrangement according to at least one embodiment of the invention has a high signal-to-noise ratio when registering electric currents.

The circuit arrangement according to at least one embodiment of the invention is suitable in particular for detecting a progressively rising current signal generated in accordance with the redox cycling principle (cf. FIG. 5). By means of suitable setting of the measurement time or the reference ranges of the electrical potential of the sensor electrodes and of the first capacitor which are relevant to the functionality of the circuit arrangement according to at least one embodiment of the invention, the number of events to be detected (e.g. in the form of pulses) can be set flexibly to the requirements of the individual case.

Preferably, the circuit arrangement has a counter element that is electrically coupled to the second circuit unit and is set up in such a way that it counts the number and/or the temporal sequence of the events. Furthermore, the circuit arrangement may be set up in such a way that a direct outputting of the sensor frequency, i.e. the frequency of the events, is provided.

In accordance with an advantageous development, the counter element is set up in such a way that it registers the temporal sequence of the events in at least two time intervals at a temporal distance from one another.

In other words, the events detected by the second circuit unit in respect of the fact that the electrical potential of the first capacitor moves outside the second reference range are counted by use of the counter element, and in particular the temporal distance between successive events is detected. Counting the temporal distances between the events corresponds to determining the frequency of the events. Thus, the analog current signal on the sensor electrode is converted into a digital signal that is contained in the frequency determined. As a result, it is possible, in particular, to achieve a high dynamic range of the circuit arrangement. Technically, it is possible, with a tenable outlay, to generate, detect and process for example frequencies of between 100 Hz and 10 MHz, so that a dynamic range of five or more decades can be achieved.

Preferably, the circuit arrangement according to at least one embodiment of the invention has a calibration device that can be coupled to the first circuit unit and serves for calibrating the circuit arrangement, which is set up in such a way that a second electrical reference potential can be applied to the first circuit unit by way of the calibration device, the second circuit unit being coupled either to the calibration device or to the sensor electrode.

The possibility of being able, according to at least one embodiment of the invention, to calibrate the circuit arrangement increases the degree of reliability of the signals registered and enables monitoring of the entirely satisfactory functionality of the circuit arrangement. Furthermore, the measurement accuracy of the circuit arrangement can be increased by way of a calibration device.

Preferably, the first circuit unit has a first comparator element having two inputs and an output, the first input being coupled to the sensor electrode in such a way that the first input is at the electrical potential of the sensor electrode, whereas the second input is brought to a third electrical reference potential, which defines the electrical desired potential. The first comparator element is set up in such a way that an electrical signal is generated at its output such that the electrical potential of the sensor electrode is held in the predeterminable first reference range around the predeterminable electrical desired potential.

The first circuit unit serves for holding constant a predeterminable voltage, referred to here as the electrical desired potential, at the sensor electrodes.

In accordance with an advantageous refinement in the case of the circuit arrangement of at least one embodiment, the first circuit unit has a variable nonreactive resistor, by which the sensor electrode can be coupled to the first capacitor of the second circuit unit in such a way that the potential of the sensor electrode is held in the predeterminable first reference range around the predeterminable electrical desired potential.

In other words, for the purpose of holding the potential of the sensor electrode constant, the coupling of the sensor electrode to the first capacitor may be realized by means of a controllable nonreactive resistor. The value of the nonreactive resistance that is presently set in each case is a measure of the present strength of the electrical coupling between the sensor electrode and the first capacitor.

Furthermore, the first circuit unit preferably has a transistor, the gate region of which is coupled to the output of the first comparator element, the first source/drain region of which is coupled to the sensor electrode and the second source/drain region of which is coupled to the first capacitor.

In other words, the transistor described functions as a control element that sets the current flow between the sensor electrode and the first capacitor.

Furthermore, the second circuit unit may have a second comparator element having two inputs and an output, the first input being coupled to the first capacitor in such a way that the first input is at the electrical potential of the first capacitor, and the second input being at a fourth electrical reference potential, which defines the second electrical reference range. The second comparator element is set up in such a way that an electrical signal is generated at its output such that, if the electrical potential of the first capacitor exceeds the fourth electrical reference potential, the first capacitor is brought to the first electrical reference potential.

As an alternative to the refinement described, the second circuit unit of the circuit arrangement has a second comparator element having two inputs and an output, the first input being coupled to the first capacitor in such a way that the first input is at the electrical potential of the first capacitor, the second input being at a fourth electrical reference potential, which defines the second electrical reference range. Furthermore, the second comparator element is set up in such a way that an electrical signal is generated at its output such that, if the electrical potential of the first capacitor falls below the fourth electrical reference potential, the first capacitor is brought to the first electrical reference potential.

The first and/or the second comparator element is preferably an operational amplifier.

The above explanations show that the elements for forming the circuit arrangement according to at least one embodiment of the invention are all electronic standard components which are expedient in production and which can be produced by standard methods. Therefore, the circuit arrangement according to the invention can be produced with little complexity.

In accordance with a preferred development of the circuit arrangement according to at least one embodiment of the invention, its second circuit unit has at least one second capacitor, the circuit arrangement being set up in such a way that either one of the at least one second capacitors or the first capacitor or at least two of the capacitors is/are simultaneously connected into the circuit arrangement.

Clearly, the circuit arrangement has a plurality of parallel-connected capacitors which have different or identical material parameters (for example capacitance C) and in each case one or a plurality of which can optionally be actively connected into the circuit arrangement. A user therefore has the possibility of selecting, in accordance with the requirements of the individual case, that or those suitable capacitors which is or are expedient with regard to measurement accuracy and desired dynamic range. Providing different capacitors, each of which can be actively connected into the circuit arrangement, increases the detection sensitivity of the circuit arrangement for registering electric currents, and likewise increases the dynamic range.

The circuit arrangement according to at least one embodiment of the invention may be designed as an integrated circuit.

In particular, the circuit arrangement of at least one embodiment of the invention may be integrated into a semiconductor substrate (e.g. a chip of a silicon wafer), or be formed partially on the semiconductor substrate. The integration of the circuit arrangement increases the sensitivity and miniaturizes the circuit arrangement. Miniaturization brings about a cost advantage since macroscopic measurement equipment is obviated. Furthermore, the circuit arrangement according to the invention can be produced by way of standardized semiconductor technology methods which likewise has a favorable effect on the production costs. Furthermore, the integration of the circuit arrangement into a semiconductor substrate enables the current signal that is to be registered to be processed on chip, i.e. in direct proximity to the sensor event. Short communication paths of the current signal keep down interference influences such as noise, etc., so that a high signal-to-noise ratio can be achieved.

At least one embodiment of the invention furthermore provides an electrochemical sensor having a circuit arrangement having the features described. The electrochemical sensor may be configured in particular as a redox recycling sensor.

As described above with reference to FIG. 4A, FIG. 4B, FIG. 4C, a sensor based on the principle of redox cycling has a sensor current characteristic that rises progressively with respect to time. Such a current signal that rises essentially monotonically with respect to time is well suited to being registered by means of the circuit arrangement according to the invention, since the progressively increasing current signal can be decomposed into charge packets that have accumulated on the first capacitor and are detected by means of pulses individually by the circuit arrangement according to the invention.

In particular, the detection sensitivity of the circuit arrangement according to at least one embodiment of the invention is high enough to register electric currents of the order of magnitude of between approximately 1 pA and approximately 100 nA, as are often generated by biosensors in accordance with the redox cycling principle with customary sensor electrode geometries.

Furthermore, at least one embodiment of the invention provides a sensor arrangement having a plurality of circuit arrangements having the features described above.

What is possible is a parallel analysis, for example the parallel registering of different DNA half strands by way of a plurality of redox cycling sensors that have different capture molecules immobilized on their sensor electrodes. A parallel analysis of a liquid to be investigated is an urgent requirement with regard to many applications in biotechnology and genetic engineering or in foodstuffs technology. A temporally parallel analysis saves time and therefore costs. Furthermore, the sensor arrangement may be set up in such a way that the individual sensor cells (formed in each case by a circuit arrangement) can be read serially.

In particular, in the case of the sensor arrangement, each of the circuit arrangements may be set up as an autonomously operating sensor element.

The circuit arrangements of the sensor arrangement may be arranged essentially in matrix form, but as an alternative also e.g. hexagonally.

Furthermore, the sensor arrangement may have a central drive circuit for driving a circuit arrangement, a central supply circuit for providing supply voltages or supply currents and/or a central read-out circuit for reading the circuit arrangements. This circuit or these circuits are preferably coupled to at least one portion of the circuit arrangements.

The method according to at least one embodiment of the invention for processing a current signal provided via a sensor electrode is described below. Refinements of the circuit arrangement, of the electrochemical sensor and of the sensor arrangement also apply to the method for processing a current signal provided via a sensor electrode.

The method according to at least one embodiment of the invention for processing a current signal provided via a sensor electrode is effected using a circuit arrangement according to at least one embodiment of the invention having the features described above. In accordance with the method, the electrical potential of the sensor electrode is held in the predeterminable first reference range around the predeterminable electrical desired potential by the first capacitor and the sensor electrode being coupled in such a way that a matching of the electrical potential is made possible. Furthermore, if the electrical potential of the first capacitor moves outside the second reference range, by way of the second circuit unit, this event is detected and the first capacitor is brought to the first electrical reference potential.

In accordance with a preferred development of the method according to at least one embodiment of the invention, the number and/or the temporal sequence of the events is counted by means of a counter element electrically coupled to the second circuit unit.

Preferably, the counter element is used to register the temporal sequence of the events in at least two time intervals at a temporal distance from one another.

Another refinement of at least one embodiment of the invention provides for the sensor electrode to be set up as a generator electrode. Furthermore, a collector electrode is provided. The circuit arrangement furthermore has a third circuit unit, which is electrically coupled to the collector electrode. A fourth circuit unit has a second capacitor. The third circuit unit is set up in such a way that it holds the electrical potential of the collector electrode in a predeterminable second reference range around a predeterminable electrical second desired potential by coupling the second capacitor and the collector electrode in such a way that a matching of the electrical potential of the collector electrode is possible.

The second circuit unit and the fourth circuit unit are set up in such a way that, if the electrical potential of the second capacitor is outside a second reference range, said circuit units detect this event and bring the second capacitor to a second electrical reference potential. The number and/or the temporal sequence of the events is counted by way of a counter element electrically coupled to the second circuit unit and the fourth circuit unit.

One advantage of at least one embodiment of this refinement is the improvement of the signal/noise ratio since the information at two electrodes is evaluated.

However, it is not absolutely necessary to measure the signals at the two electrodes independently of one another. Therefore, two further embodiments are specified which evaluate the sum (more precisely: the sum in terms of absolute value) of the signals at the two electrodes, i.e. at the generator electrode and at the collector electrode. Clearly, these refinements of the invention are based on the insight that in the redox cycling method, the electric currents at the two electrodes, that is to say at the generator electrode and at the collector electrode, in principle carry the same information and therefore do not have to be processed separately. Restricting the evaluation to one signal would impair the signal/noise ratio, however.

The expression "sum" is to be understood in such a way as to also encompass the case in which, for example for test purposes and for fundamental investigations, the circuits also afford the possibility of measuring the electrodes individually (but not simultaneously) and evaluating the signals thereof in the respective circuit.

These refinements of at least one embodiment of the invention make it possible, as will be explained in more detail below, to save a comparator and a counter element. Thus, it makes it possible to considerably reduce the area required for the sensor and the evaluation circuit on a chip. This permits the construction of considerably denser sensor arrays.

In accordance with the first refinement of at least one embodiment of the invention for measuring the summation signal, a third capacitor coupled to the first capacitor is provided, said third capacitor having a greater capacitance than the first capacitor, the first capacitor and the third capacitor forming a capacitive first voltage divider. Furthermore, a fourth capacitor coupled to the second capacitor is provided, the fourth capacitor having a greater capacitance than the second capacitor. The second capacitor and the fourth capacitor form a capacitive second voltage divider.

Preferably, the capacitance of the third capacitor is greater than the capacitance of the first capacitor at least by a factor of two and the capacitance of the fourth capacitor is greater than the capacitance of the second capacitor at least by a factor of two. Particularly preferably, the capacitance of the third capacitor is greater than the capacitance of the first capacitor at least by a factor of ten and the capacitance of the fourth capacitor is greater than the capacitance of the second capacitor likewise at least by a factor of ten.

Clearly, in accordance with at least one embodiment of this refinement, the current for the generator electrode is thus drawn from the first capacitive voltage divider and the current for the collector electrode is drawn from the capacitive second voltage divider. For the case where the capacitance of the third capacitor is considerably greater than that of the first capacitor and the capacitance of the fourth capacitor is considerably greater than that of the second capacitor, the potential, that is to say the voltage swing, on the nodes on both sides of the third capacitor and of the fourth capacitor, respectively, is essentially identical since the two nodes are capacitively strongly coupled.

The second circuit unit and the fourth circuit unit jointly have a summation comparator element having two inputs and an output,
- a first input being connected between the first capacitor and the third capacitor,
- a second input being connected between the second capacitor and the fourth capacitor, and
- the output being coupled to a counter element, which is set up in such a way that it counts the number and/or the temporal sequence of the events.

The second refinement of the invention for measuring the summation signal provides for
- the generator electrode, as described above, to be connected to a first circuit unit for regulating the electrical potential; furthermore, by way of a first capacitor and a second circuit unit, as described above, a first pulse sequence is generated at the output of the second circuit unit;
- the collector electrode, as described above, to be connected to a third circuit unit for regulating the electrical potential; furthermore, by way of a second capacitor and a fourth circuit unit, a second pulse sequence is generated at the output of the fourth circuit unit.

Furthermore, a synchronization element having two inputs and an output is provided,
- the first pulse sequence, i.e. the first signal, being present at a first input, i.e. the first input being coupled to the output of the second circuit unit,
- the second pulse sequence, i.e. the second signal, being present at a second input, i.e. the second input being coupled to the output of the fourth circuit unit.

The synchronization element is set up in such a way that, in the case of overlapping pulses, i.e. signals that overlap one another, one of the pulse sequences is delayed to an extent such that the overlap is resolved. Two overlapping pulses at the inputs thus give rise to a double pulse at the output of the synchronization element.

The synchronization element preferably has a buffer memory.

BRIEF DESCRIPTION OF THE DRAWINGS

Example embodiments of the invention are illustrated in the figures and are explained in more detail below.
In the figures:
FIG. 6A shows a schematic view of a circuit arrangement in accordance with a second example embodiment of the invention,
FIG. 6B shows a schematic view of a circuit arrangement in accordance with a third example embodiment of the invention,
FIG. 7 shows a block diagram of a circuit arrangement in accordance with a fourth example embodiment of the invention,
FIG. 8 shows a block diagram showing the construction of a first circuit unit (voltage regulator) shown in FIG. 7,
FIG. 12 shows an example embodiment of the sensor arrangement according to at least one embodiment of the invention.
FIG. 13 shows a circuit arrangement in accordance with a first example embodiment of the invention;
FIG. 14 shows a circuit arrangement in accordance with a second example embodiment of the invention;
FIGS. 15a and 15b show voltage profiles at the nodes K1 to K4 from the circuit arrangement in accordance with FIG. 14 against the time (FIG. 15b) and the reset pulse (FIG. 15a)

DETAILED DESCRIPTION OF THE EXAMPLE EMBODIMENTS

A first preferred example embodiment of the circuit arrangement according to the invention is described below with reference to FIG. 1.

Figure 1:
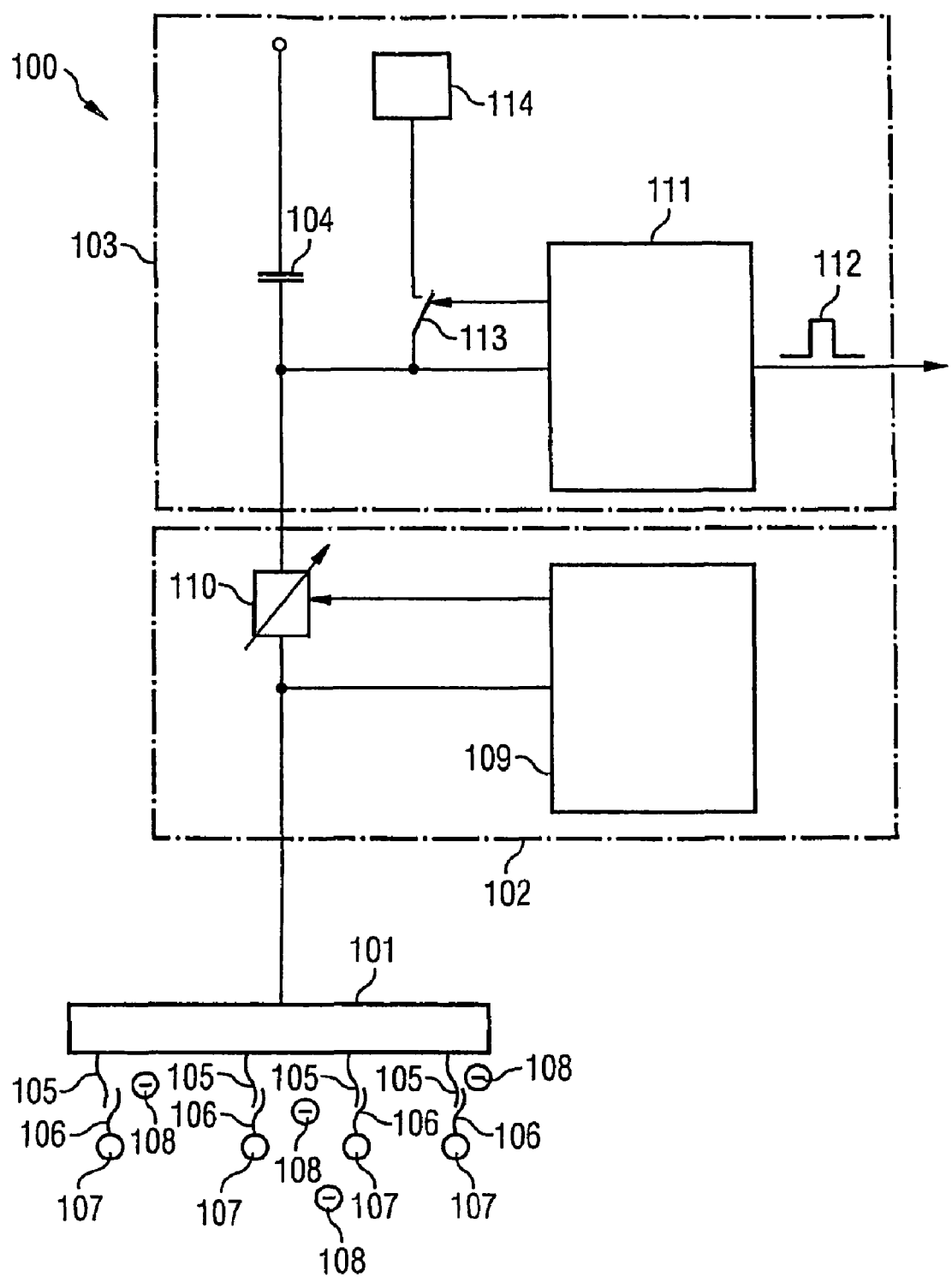
FIG. 1 shows a schematic view of a circuit arrangement in accordance with a first example embodiment of the invention.
Figure 2A:
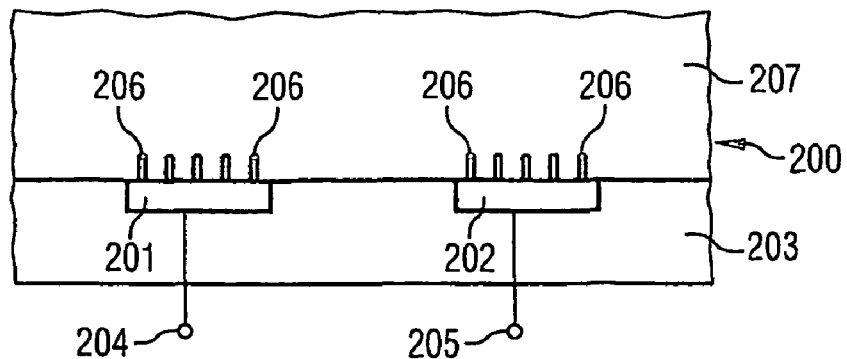
FIG. 2A shows a cross-sectional view of a sensor in accordance with the prior art in a first operating state.
Figure 2B:
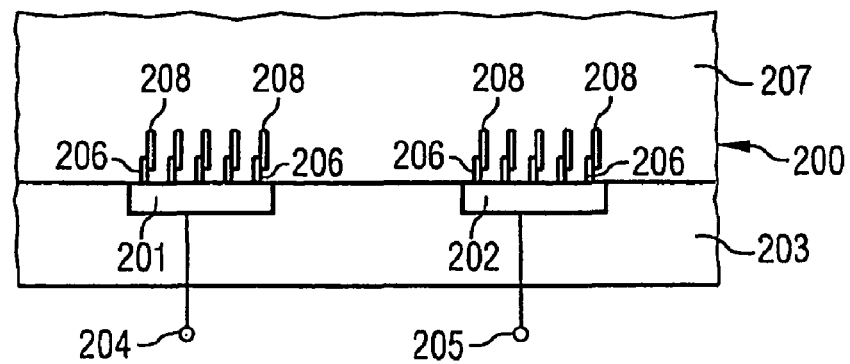
FIG. 2B shows a cross-sectional view of the sensor in accordance with the prior art in a second operating state.
Figure 3A:
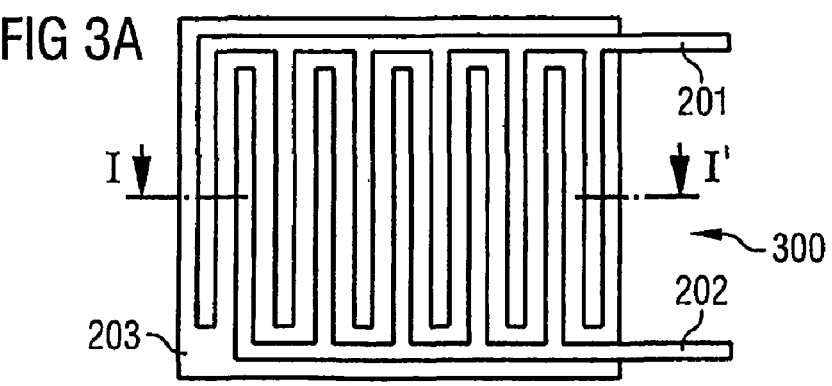
FIG. 3A shows a plan view of interdigital electrodes in accordance with the prior art.
Figure 3B:
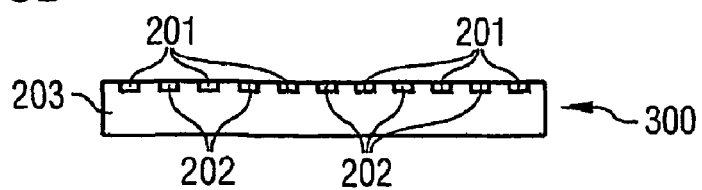
FIG. 3B shows a cross-sectional view along the section line I-I' of the interdigital electrodes in accordance with the prior art as shown in FIG. 3A.

The circuit arrangement 100 shown in FIG. 1 has a sensor electrode 101, a first circuit unit 102, which is electrically coupled to the sensor electrode 101, and a second circuit unit 103, which has a first capacitor 104. The first circuit unit 102, illustratively a potentiostat, is set up in such a way that it holds the electrical potential of the sensor electrode 101 in a predeterminable first reference range around a predeterminable electrical desired potential by coupling the first capacitor 104 and the sensor electrode 101 in such a way that a matching of the electrical potential is made possible (by way of a current flow for control). Furthermore, the second circuit unit 103 is set up in such a way that, if the electrical potential of the first capacitor 104 is outside a second reference range, said second circuit unit detects this event and brings the first capacitor 104 to a first electrical reference potential.

As is furthermore shown in FIG. 1, capture molecules 105 are immobilized on the surface of the sensor electrode 101. The capture molecules 105 from FIG. 1 have hybridized with molecules 106 to be registered, each of the molecules 106 to be registered having an enzyme label 107.

Figure 4A:
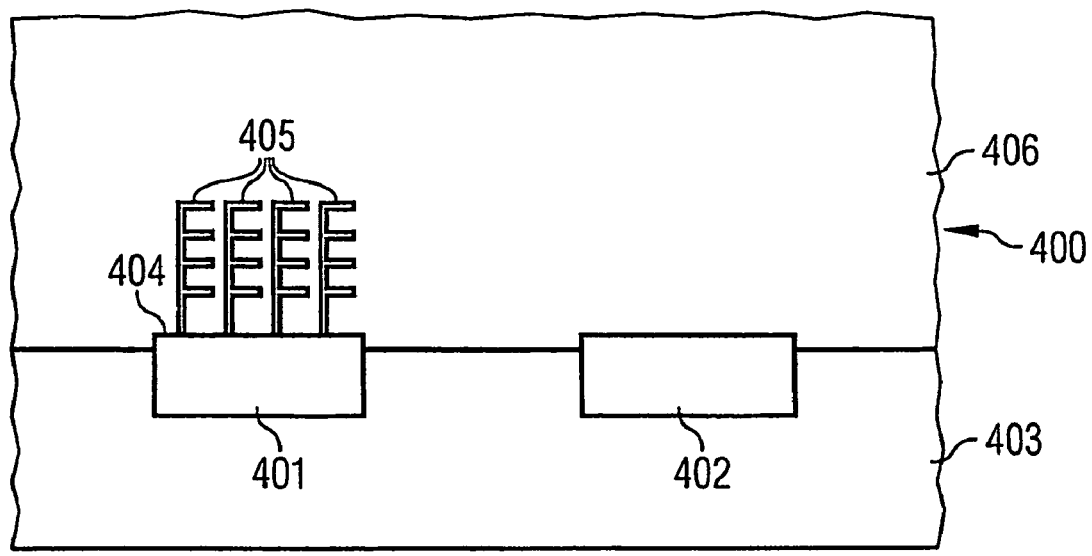
FIG. 4A shows a biosensor based on the principle of redox recycling in a first operating state in accordance with the prior art.
Figure 4B:
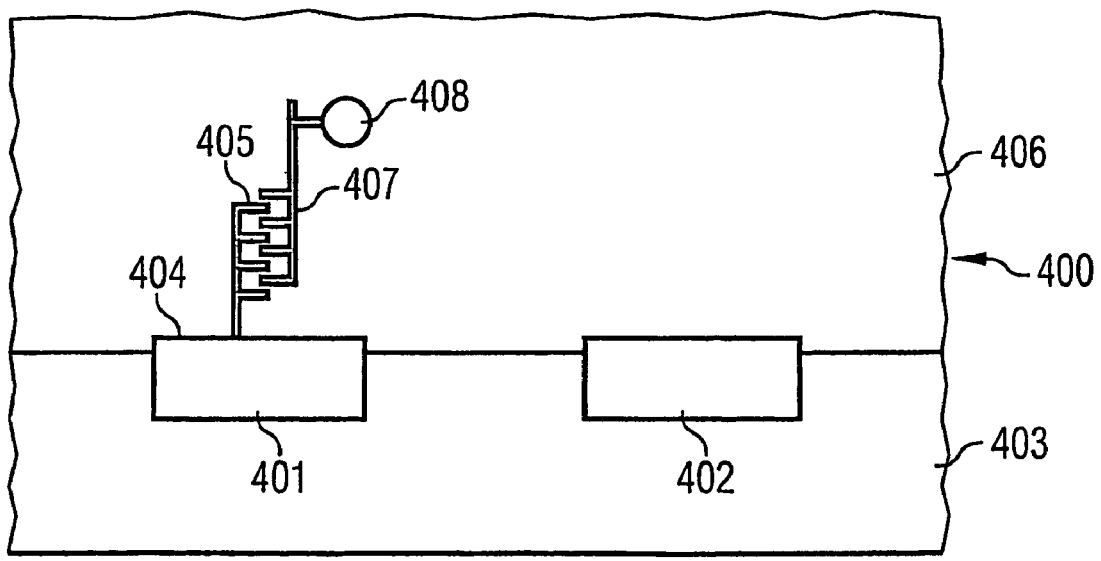
FIG. 4B shows a biosensor based on the principle of redox recycling in a second operating state in accordance with the prior art.
Figure 4C:
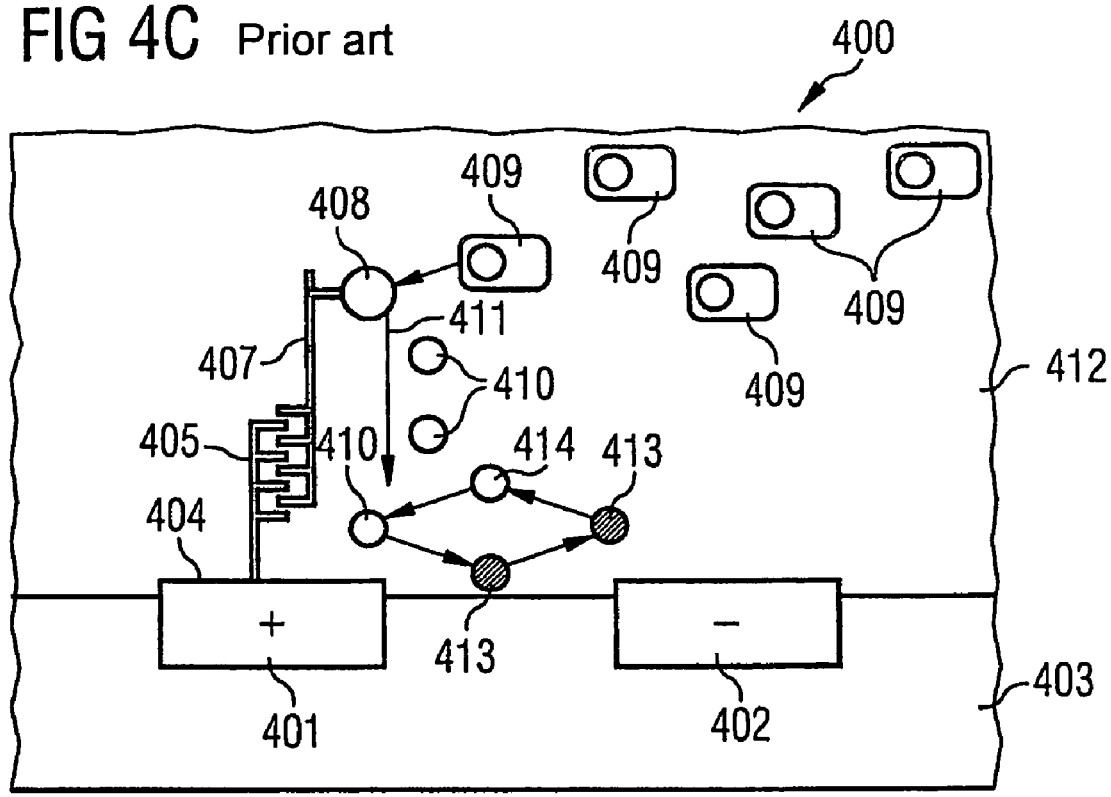
FIG. 4C shows a biosensor based on the principle of redox cycling in a third operating state in accordance with the prior art.

The sensor electrode 101 with the capture molecules immobilized thereon as shown in FIG. 1 functions according to the principle of redox cycling (cf. FIG. 4A, FIG. 4B, FIG. 4C). Therefore, FIG. 1 shows electrically charged particles 108, which are generated by way of the enzyme label 107 in the liquid to be investigated and which generate an electric sensor current that is coupled into the circuit arrangement 100 from the first sensor electrode 101.

This sensor current alters the electrical potential of the sensor electrode 101 in a characteristic manner. This electrical potential is present at the input of a first control unit 109 of the first circuit unit 102. The first circuit unit 102 and in particular the first control unit 109 ensure that the sensor electrode 101 remains at a predeterminable, constant electrical potential by carrying out a shift of charge carriers between the first capacitor 104 and the sensor electrode 101 when there is a sufficiently great deviation of the sensor electrode potential from the electrical desired potential.

This is indicated schematically in FIG. 1 by way of the controllable nonreactive resistor 110, which can be controlled by the first control unit 109. The circuit block shown is an analog control loop that controls the current flow between the capacitor 104 and the sensor electrode 101 in such a way that the voltage at the sensor electrode 101 remains constant. A continuous control of the current flow is made possible by way of the controllable resistor 110.

If the electrical potential of the sensor electrode 101 moves outside the first reference range on account of a sufficiently large number of sensor events at its surface, then the first circuit unit 102 and in particular the first control unit 109 ensure that the current flow between the sensor electrode 101 and the first capacitor 104 increases or decreases, thereby enabling a matching of the electrical potential between the first capacitor 104 and the sensor electrode 101. Clearly, the resistance of the controllable resistor 110 is thus increased or decreased by way of the first control unit 109 of the first circuit unit 102, thereby enabling a current flow between the sensor electrode 101 and the first capacitor 104. In this scenario, electrical charge can flow back and forth between the first capacitor 104 and the sensor electrode 101.

If the electrical potential of the first capacitor 104 moves outside a second reference range on account of this charge shift, then this event is detected by the second circuit unit 103 and in particular by a second control unit 111, which preferably has a comparator, of the second circuit unit 103. As shown in FIG. 1, this detection may consist in an electrical pulse 112 being generated at an output of the second control unit 111.

Furthermore, if the electrical potential of the first capacitor 104 moves outside the second reference range, the first capacitor 104 is brought to the first electrical reference potential by way of the second circuit unit 103 and in particular by means of the second control unit 111 of the second circuit unit 103. This is indicated in FIG. 1 in that a further switch 113 is closed on account of a signal initiated by the second control unit 111 of the second circuit unit 103, as a result of which the first capacitor 104 is electrically coupled to a voltage source 114, as a result of which the first capacitor 104 is brought to the first electrical reference potential defined by way of the voltage source 114.

A basic idea of the circuit arrangement according to at least one embodiment of the invention may clearly be seen in the fact that a sensor current to be registered is converted into a frequency proportional to the current without prior analog amplification. By way of the circuit arrangement according to at least one embodiment of the invention, the potential at the sensor electrode is held constant and the electrical charge required for this (having a positive or negative sign) is drawn from a capacitor having the capacitance C. Owing to the charge drawn $\Delta Q$ $$\Delta Q = \int I dt \quad (1)$$

on account of a current flow I between the first capacitor and the sensor electrode integrated over the time t, the voltage $\Delta U$ present at the first capacitor changes in accordance with the relationship $$\Delta Q = C \Delta U \quad (2)$$

The voltage present at the capacitor is monitored by way of a threshold value circuit. If a specific value is exceeded or undershot, then the circuit initiates a digital pulse by means of which a switch is closed, as a result of which the electrical voltage at the capacitor is reset to a predetermined value. What is obtained as a result, in measurement operation, is a pulse sequence from the threshold value circuit whose frequency is proportional to the signal current.

As described above with reference to FIG. 1, the circuit arrangement according to at least one embodiment of the invention, for operating an electrochemical sensor, essentially has two circuit units. The first circuit unit monitors the electrical potential (i.e. the voltage with respect to a reference point) present at the sensor electrode. By way of example, an operational amplifier may be used to compare the electrical potential of the sensor electrode with a reference potential, and to control the electric current flow between the sensor electrode and the first capacitor in such a way that the electrical potential of the sensor electrode remains constant.

The counter-current required for matching the sensor current is drawn, as described, from the first capacitor of the second circuit unit. The voltage at the first capacitor is monitored by a threshold value circuit, for example a comparator circuit, in the second circuit unit. In the case where a second reference range of the electrical potential of the first capacitor is exceeded or undershot, the second circuit unit outputs a reset pulse. This digital pulse, which preferably has a fixed temporal length, resets the potential of the capacitor (or the electrical voltage between the two capacitor plates) to a first electrical reference potential. The pulse should have a constant length since the counter-current is drawn from a voltage source during this time. This dead time reduces the measured frequency and, insofar as the dead time is not negligibly short, has to be taken into account in the evaluation of the data.

In order, in a scenario in which the dead time is not negligible or is intended to be compensated for, to minimize the measurement error as a result of the resetting of the circuit, it is possible to provide two (or more) capacitors that are operated alternately in the manner described. If one (active) capacitor is charged by the sensor current, then the other (passive) capacitor is reset to the first electrical reference potential in this time interval. If the potential at the active capacitor exceeds the predetermined value, then, preferably, a reset pulse is not initiated immediately by the second circuit unit 103, rather firstly a changeover is made between the two capacitors and only afterward is the now passive capacitor reset. By means of this procedure, the sensor current is not drawn directly from a voltage source at any point in time, but rather always from a capacitor that serves as a charge reservoir.

Referring to FIG. 1 again, the reset process is preferably effected by way of a switching transistor that discharges (for example completely discharges) the first capacitor to a predeterminable potential in the reset phase. The first electrical reference potential is preferably a ground potential. The sensor current subsequently charges the first capacitor again. The temporal dependence of the electrical voltage at the first capacitor can be described by the following expression:

$$U(t) = 1/C \int_0^t I_{Sensor} dt' \quad (3)$$

The sensor current $I_{sensor}$ derived from the sensor electrode has, as described above with reference to FIG. 5, a constant offset component $I_{offset}$ and a signal current that rises (ideally) linearly with time:

$$I_{sensor} = I_{offset} + mt \quad (4)$$

If equation (4) is inserted into equation (3) and the integral is calculated, then the electrical voltage which builds up between a first instant $t_1$ and a second instant $t_2$ turns out to be:

$$U(t) = 1/C(I_{offset}[t_2-t_1] + m/2[t_2^2 - t_1^2]) \quad (5)$$

The time interval $\Delta t$ in which a specific voltage difference $\Delta U$ is built up is therefore:

$$\Delta t = t_2 - t_1 = (C\Delta U)/(I_{offset} + mt) \quad (6)$$

In this case, t is the mean time of the interval considered, i.e.:

$$t = (t_1 + t_2)/2 \quad (7)$$

The frequency f measured within a sufficiently short interval $\Delta t$ disregarding a dead time $t_{dead}$ during resetting of the capacitor ($t_{dead} \ll \Delta t$) accordingly turns out to be:

$$f = \Delta t^{-1} = I_{offset}/(C\Delta U) + mt/(C\Delta U) \quad (8)$$

This frequency f may be conducted away as a digital signal directly from the circuit arrangement (for example from a chip if the circuit arrangement is integrated into a semiconductor substrate) and be processed further and evaluated. Equation (8) shows that the frequency f has a constant component attributed to the offset current $I_{offset}$ of the sensor electrode. The second term in (8) represents the frequency component that rises linearly with time (the assumption of a current signal that rises exactly linearly is idealizing, of course), is attributed to sensor events in accordance with the redox cycling principle, and includes the actual measurement variable m.

The metrologically relevant variable m is obtained by carrying out for example two period or frequency measurements with a predetermined time distance $\Delta t_{meas} = t_B - t_A$. If $t_A$ and $t_B$, respectively, are inserted into equation (8) and the frequencies $f_A$ and $f_B$ obtained therefrom are subtracted from one another, then the frequency difference $\Delta f$ obtained is:

$$\Delta f = f_B - f_A = m\Delta t_{meas}/(C\Delta U) \quad (9)$$

The metrologically relevant variable m results from this as:

$$m = \Delta f C \Delta U / \Delta t_{meas} \quad (10)$$

Figure 5:
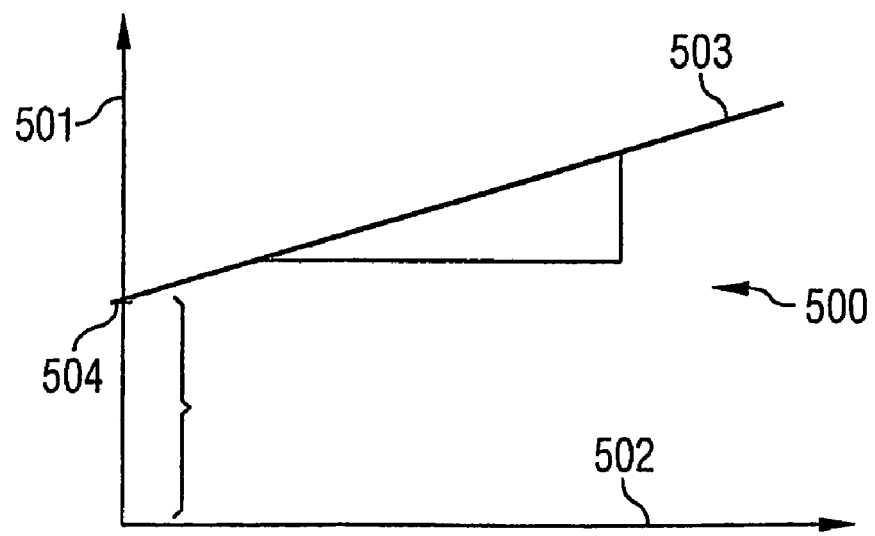
FIG. 5 shows a functional profile of a sensor current in the context of a redox cycling process.

Accordingly, from two measurements of the output frequency of the sensor, it is possible to directly determine the metrologically relevant variable m, clearly the gradient of the current-time curve profile 503 from FIG. 5.

As an alternative to the frequency or period duration measurement described, it is possible for the pulses of the second circuit unit to be provided to the input of a counter element that sums the number or the temporal sequence of the pulses and preferably converts this into a binary word coding the number of elapsed time intervals $\Delta t$.

Such a counter element may count the reset pulses of the first capacitor for a predetermined length of time, digitally output the counter reading after an external pulse and then reset the counter element.

The counter reading n of the counter element of the circuit arrangement after the time period $t_{count} = t_{c2} - t_{c1}$ defined by way of the instants $t_{c1}$ and $t_{c2}$ has elapsed is calculated to a good approximation as:

$$n = \int_{t_{c1}}^{t_{c2}} f dt \quad (11)$$

$$= I_{offset}(t_{c2} - t_{c1})/(C\Delta U) + m(t_{c2}^2 - t_{c1}^2)/(2C\Delta U)$$

In accordance with the explanations above referring to the determination of m from frequency measurements, at least two measurements of the counter readings n are necessary, from which both $I_{offset}$ and the metrologically relevant variable m can be determined by way of equation (11).

One advantage of integrating a counter element into the circuit arrangement of at least one embodiment of the invention is the resultant temporal averaging of the measurement result that is effected automatically. Since, in the case of the small sensor currents that are to be expected—particularly in the detection of biomolecules—, fluctuations in the instantaneous value of the measurement variable are possible (for example owing to noise effects, etc.), an averaging is particularly advantageous.

In accordance with an example embodiment of the circuit arrangement according to the invention, the second circuit unit has at least one second capacitor, the circuit arrangement being set up in such a way that either one of the at least one second capacitors or the first capacitor or at least two of the capacitors is/are simultaneously connected into the circuit arrangement.

In order to extend the dynamic range and in order to improve the measurement accuracy, provision is made, illustratively, of a storage capacitance that can be changed over. If the sensor electrode supplies an increased electric sensor current, which would result in an increased output frequency, a further capacitor, for example, may be connected in parallel with the first capacitor. This reduces the output frequency and thus possible measurement inaccuracies on account of the dead time during resetting of the first capacitor. In addition to the measurement range switching realized in this way, it is also possible to vary the interval $\Delta U$ within which the capacitor voltage oscillates. This permits a continuous tuning of the measurement range.

A circuit arrangement 600 in accordance with a second preferred example embodiment of the invention is described below with reference to FIG. 6A.

The circuit arrangement 600 has a sensor electrode 601, a first circuit unit 602, which is coupled to the sensor electrode 601, and a second circuit unit 603, which has a first capacitor 604. The first circuit unit 602 is set up in such a way that it holds the electrical potential of the sensor electrode 601 in a predeterminable first reference range around a predeterminable electrical desired potential by coupling the first capacitor 604 and the sensor electrode 601 in such a way that a matching of the electrical potential is made possible. Furthermore, the second circuit unit 603 is set up in such a way that, if the electrical potential of the first capacitor 604 is outside a second reference range, said second circuit unit detects this event and brings the first capacitor 604 to a first electrical reference potential, provided by the first voltage source at the node 605, of the second circuit unit 603.

Furthermore, the circuit arrangement 600 has a counter element 606, which is electrically coupled to the second circuit unit 603 and is set up in such a way that it counts the number and the temporal sequence of the events.

Furthermore, the first circuit unit 602 has a first comparator element 607 having two inputs and an output, the first input being coupled to the sensor electrode 601 in such a way that the first input is at the electrical potential of the sensor electrode 601. The second input is brought to a third electrical reference potential, which defines the electrical desired potential (or the first electrical reference range). The third electrical reference potential, the potential of the second input of the first comparator element 607, is provided by a second voltage source 608. Furthermore, the first comparator element 607 is set up in such a way that an electrical signal is generated at its output such that the electrical potential of the sensor electrode 601 is held in the predeterminable first reference range around the predeterminable electrical desired potential.

As is furthermore shown in FIG. 6A, the first circuit unit 602 has a transistor 609, the gate region of which is coupled to the output of the first comparator element 607, the first source/drain region of which is coupled to the sensor electrode 601 and the second source/drain region of which is coupled to the first capacitor 604.

Clearly, the field-effect transistor 609 is a variable nonreactive resistor (controllable by the first comparator element 607) by which the sensor electrode 601 can be coupled to the first capacitor 604 of the second circuit unit 603 in such a way that the electrical potential of the sensor electrode 601 is held in the predeterminable first reference range around the predeterminable electrical desired potential. In other words, any intermediate value between complete coupling and complete decoupling of sensor electrode 601 and capacitor 604 can be set by means of the transistor 609.

Furthermore, the second circuit unit 603 has a second comparator element 610 having two inputs and an output, the first input being coupled to the first capacitor 604 in such a way that the first input is at the electrical potential of the first capacitor 604, and the second input being at a fourth electrical reference potential provided by a third voltage source 611. The fourth electrical reference potential defines the second electrical reference range.

The second comparator element 610 is set up in such a way that an electrical signal is generated at its output such that, if the electrical potential of the first capacitor 604 exceeds the fourth electrical reference potential, the first capacitor 604 is brought to the first electrical reference potential. For this purpose, the second circuit unit 603 provides the switch 612 (which may be designed as a transistor, for example) with an electrical signal such that the switch 612 is closed and an electrical coupling is produced between the first voltage source 605 and the first capacitor 604.

Furthermore, a pulse transmitter 613 is connected to the output of the second comparator 610, and detects the event that the electrical potential of the first capacitor 604 is outside the second reference range, and outputs a digital pulse having a defined length τ.

As is furthermore shown in FIG. 6A, this pulse signal of the pulse transmitter 613 is provided to the counter element 606, which counts the number of pulses and the temporal sequence thereof (i.e. the frequency at which the pulses arrive).

The first comparator element 607 and the second comparator element 610 of the circuit arrangement 600 are in each case configured as an operational amplifier.

The basic circuit diagram of the circuit arrangement 600 according to at least one embodiment of the invention as shown in FIG. 6A thus has a potentiostat unit realized by use of the first circuit unit 602 and by use of the first capacitor 604, respectively. This holds the electrical potential of the sensor electrode 601 at the electrical desired potential in the first reference range, defined by way of the third electrical reference potential. The sensor current derived from the sensor electrode 601 is drawn from the second circuit unit 603, which furthermore functions as a current-frequency converter. The first capacitor 604 subsequently supplies electrical charge to the sensor electrode 601 for the purpose of holding the electrical potential thereof, the electrical voltage present at the first capacitor 604 being monitored by way of the comparator circuit described.

If the electrical voltage of the first capacitor 604 falls below a threshold value, then the comparator 610 or the pulse transmitter 613 initiates a pulse having the defined length τ, which, by means of the switch 612, subjects the first capacitor 604 to charge reversal to the electrical potential of the first voltage source 605. The pulse furthermore serves as a counting pulse for the counter element 606 coupled to the output of the second comparator element 610.

It must be emphasized that the circuit arrangement 600 shown in FIG. 6A is set up in such a way that it provides the sensor electrode 601 with electric currents; the sensor electrode 601 in this case operates as a current sink. By contrast, if electric currents generated at the sensor electrode 601 are intended to be taken up by the circuit arrangement 600, the latter would have to be constructed complementarily.

A third preferred example embodiment of the circuit arrangement according to the invention is described below with reference to FIG. 6B. Those elements of the circuit arrangement 620 which correspond to the circuit arrangement 600 shown in FIG. 6A and described above are provided with the same reference symbol. Only those components of the circuit arrangement 620 which deviate from the circuit arrangement 600 shown in FIG. 6A are described in more detail below.

The circuit arrangement 620 has a calibration device 621 that can be coupled to the first circuit unit 602 and serves for calibrating the circuit arrangement 620, which is set up in such a way that a second electrical reference potential can be applied to the first circuit unit 602 by way of the calibration device 621, the first circuit unit 602 being coupled either to the calibration device 621 or to the sensor electrode 601.

What is particularly advantageous about the circuit arrangement 620 shown in FIG. 6B is that the sensor electrode 601 can optionally be decoupled from the first circuit unit 602 and can instead be coupled to the calibration device 621, a reference current source 621a being the essential component thereof. A calibration of the circuit arrangement 620 may be performed by means of a calibration current generated by the calibration device 621. This is advantageous particularly when the exact value of the capacitance C of the first capacitor 604 is not known.

In addition to statistical fluctuations of the capacitance of the first capacitor 604 owing to variations in the process technology during the method for producing the first capacitor 604, the parasitic capacitances of the circuit arrangement 620, which can be calculated only with great complexity or cannot at all be calculated exactly, make a significant contribution to the total capacitance of the storage node and critically influence the resulting output frequency in which the current signal to be registered is coded. Offset voltages, in particular of the second comparator 610 in the current-frequency converter, and possible leakage currents also have a direct influence on the output frequency to be registered.

As shown in FIG. 6B, the calibration device 621 has a reference current source 621a that can be connected in, provides a known sensor current, or increases or reduces the latter by a specific magnitude if the reference current source 621a is connected in parallel with the sensor. The change in frequency resulting on account of the connecting-in then serves for calibrating the circuit arrangement 620. Such calibration may be carried out in particular before an analyte is applied to the sensor electrode 601. In this case, the sensor electrode 601 does not supply a signal current originating from sensor events, and the output frequency is determined by the reference current of the reference current source 621a.

The optional connection either of the sensor electrode 601 or of the calibration device 621 to the first circuit unit 602 is realized by way of a further switch 622. The switch 622 may be changed over in such a way that the calibration device 621 is connected to the second circuit unit 602 in the operating state shown in FIG. 6B, whereas the sensor electrode 601 is not connected to the first circuit unit 602 in the operating state shown in FIG. 6B. In a complementary scenario corresponding to a changeover of the further switch 622 shown in FIG. 6B, the sensor electrode 601 is connected to the first circuit unit 602, whereas the calibration device 621 is not connected into the first circuit.

A fourth preferred example embodiment of the circuit arrangement 700 according to the invention is described below with reference to FIG. 7. Those components or blocks from FIG. 7 which have a direct counterpart in FIG. 6B are designated in FIG. 7 by the same reference numerals as in FIG. 6B.

FIG. 7 illustrates an embodiment of a sensor unit such as may be used in a matrix-type arrangement of a plurality of sensor units.

FIG. 7 shows the sensor electrode 601. Furthermore, FIG. 7 shows a further sensor electrode 701. The sensor electrode 601 is coupled to a first electrical node 702. The first electrical node 702 is coupled to the inverted input of the first circuit unit 602 (functionally a voltage regulator or potentiostat, also referred to as control element 602 hereinafter). Furthermore, the first electrical node 702 is coupled to one source/drain region of a first transistor 703.

The other source/drain region of the first transistor 703 is coupled to a second electrical node 704. The second electrical node 704 is coupled to the reference current source 621a of the calibration device. The gate region of the first transistor 703 is coupled to a first voltage supply 705. The first voltage supply 705 and the first transistor 703 form the further switch 622. The noninverted input of the control element 602, which inter alia contains an operational amplifier, is coupled to a third electrical node 706. The third electrical node 706 is identical to a fourth electrical node 707. "Identical" in this sense means "electrically identical", i.e. that the electrical node 706 and the electrical node 707 are (approximately) at the same electrical potential.

The fourth electrical node 707 is furthermore coupled to a first capacitance 708 and also to the second voltage source 608. The further electrode 701 is coupled to a fifth electrical node 709. The fifth electrical node 709 is identical to a sixth electrical node 710. The sixth electrical node 710 is coupled to a second capacitance 711. Furthermore, the sixth electrical node 710 is coupled to a second voltage supply 712. The output of the first control element 602 is coupled to a seventh electrical node 713.

The seventh electrical node 713 is coupled to the inverted input of the second comparator element 610, which is designed as an operational amplifier. The noninverted input of the second comparator element 610 is coupled to an eighth electrical node 714. The eighth electrical node 714 is coupled to a third capacitance 715. Furthermore, the eighth electrical node 714 is identical to a ninth electrical node 716. The ninth electrical node 716 is coupled to the third voltage source 611. Furthermore, the output of the comparator element 610 is coupled to a tenth electrical node 717.

The tenth electrical node 717 is coupled to the gate region of the switch 612, which switch 612 is designed as a transistor. One source/drain region of the switch 612 is coupled to an eleventh electrical node 718. The eleventh electrical node 718 is identical to the seventh electrical node 713—and is coupled to the first capacitor 604. The other source/drain region of the switch 612 is coupled to a twelfth electrical node 719. The twelfth electrical node 719 is on the one hand coupled to the first capacitor 604 and on the other hand identical to a thirteenth electrical node 720. The thirteenth electrical node 720 is coupled to a fourth capacitance 721 and to a fifth capacitance 722. The positive operating voltage is present at the node 720.

Furthermore, the circuit arrangement 700 has a first voltage supply unit 723 and a second voltage supply unit 724. A first and a second terminal of the first voltage supply unit 723 are coupled to two further terminals of the control element 602 and these further terminals are furthermore coupled to two terminals of the second voltage supply unit 724. A further terminal of the second voltage supply unit 724 is coupled to a fourteenth electrical node 725. The fourteenth electrical node 725 is coupled both to a further terminal of the control element 602 and to a further terminal of the comparator element 610. A further terminal of the second voltage supply unit 724 is coupled to a fifteenth electrical node 726. The fifteenth electrical node 726 is coupled to a third voltage supply 727.

Furthermore, the counter element 606 is shown in FIG. 7. The counter element 606 is coupled to a fourth voltage supply 728. The counter element 606 has a first control signal 729, a second control signal 730, a third control signal 731, a fourth control signal 732, a fifth control signal 733, a sixth control signal 734 and a seventh control signal 735. Furthermore, the counter element 606 has a counter unit 736.

The first control signal 729 is coupled to a sixteenth electrical node 737. The sixteenth electrical node 737 is coupled to an input of the counter unit 736. The second control signal 730 is coupled to a seventeenth electrical node 738. The seventeenth electrical node 738 is coupled to a further input of the counter unit 736. The third control signal 731 is coupled to an eighteenth electrical node 739.

The eighteenth electrical node 739 is coupled to a further input of the counter unit 736. The fourth control signal 732 is coupled to a nineteenth electrical node 740. The nineteenth electrical node 740 is coupled to a further input of the counter unit 736. The fifth control signal 733 is coupled to a twentieth electrical node 741. The twentieth electrical node 741 is coupled to a further input of the counter unit 736. The sixth control signal 734 is coupled to a twenty-first electrical node 742.

The twenty-first electrical node 742 is coupled to a further input of the counter unit 736. The seventh control signal 735 is coupled to a twenty-second electrical node 743. The twenty-second electrical node 743 is coupled to a sixth capacitance 744. Furthermore, the twenty-second electrical node 743 is identical to a twenty-third electrical node 745. The twenty-third electrical node 745 is coupled to a seventh capacitance 746. A signal in which the counter reading is coded is present at the output of the counter unit 736. This signal is provided to a twenty-fourth electrical node 747. The counter reading signal is communicated serially from the twenty-fourth electrical node 747 to an output terminal 748.

To summarize, components of the circuit arrangement 700 shown in FIG. 7 are the two sensor electrodes 601, 701, the first circuit unit 602, the first capacitor 604—serving as storage capacitance—with the switch 612 connected in parallel therewith, said switch being designed as a transistor and serving for resetting the capacitor voltage. This resetting is initiated by means of the second comparator element 610, which is likewise designed as an operational amplifier and which compares the voltage across the first capacitor 604 with the voltage signal of the third voltage source 611 and correspondingly drives the switch 612 designed as a transistor.

It must be emphasized that an independent circuit block for generating a pulse having a constant length is not provided in the realization shown in FIG. 7. A suitable temporal pulse duration results, on account of the circuit shown, automatically from the reaction time of the system "second comparator element 610—first capacitor 604—switch 612" and has values that are sufficiently constant over a large measurement range.

The pulses of the second comparator element 610 are counted in the counter unit 736 of the counter element 606. By way of the control signals, the counter unit 736 can be changed over to a shift register operation, as a result of which the present counter reading is output serially at the output terminal 748.

The circuitry configuration of the first comparator element 607 in the circuit arrangement 700 shown in FIG. 7 is described in more detail below with reference to FIG. 8. Those components shown in FIG. 8 which have a counterpart in FIG. 7 or FIG. 6B, respectively, are provided with the same reference numerals.

FIG. 8 shows the first control element 602 (also referred to as first circuit unit 602). The first electrical node 702 from FIG. 7 is coupled to a first electrical node 801 and the first electrical node 801 is coupled to the noninverted input of the operational amplifier 607 (of the first comparator element 607). The third electrical node 706 from FIG. 7 is coupled to the inverted input 803 of the operational amplifier 607.

Furthermore, the operational amplifier 607 is coupled to a first terminal 804a, a second terminal 804b and a third terminal 804c. The first terminal 804a is coupled to the second voltage supply unit 724. The second terminal 804b and the third terminal 804b are respectively coupled to the first voltage supply unit 823.

An output 805 of the operational amplifier 607 is coupled to a second electrical node 806. The second electrical node 806 is coupled to a capacitor 807. The capacitor 807 is coupled to a third electrical node 808. The third electrical node 808 is identical to the first electrical node 801. Furthermore, the second electrical node 806 is coupled to the gate region of the transistor 609. One source/drain region of the transistor 609 is coupled to the third electrical node 808 and the other source/drain region of the transistor 609 is coupled to an output terminal 810, which output terminal 810 corresponds to the output of the first control element 602 in FIG. 7.

The circuitry construction of the operational amplifier 607 from FIG. 8 is described in more detail below with reference to FIG. 9. The inputs and outputs or the terminals of the operational amplifier 607 that are shown in FIG. 8 are provided with the same reference numerals in FIG. 9.

Figure 9:
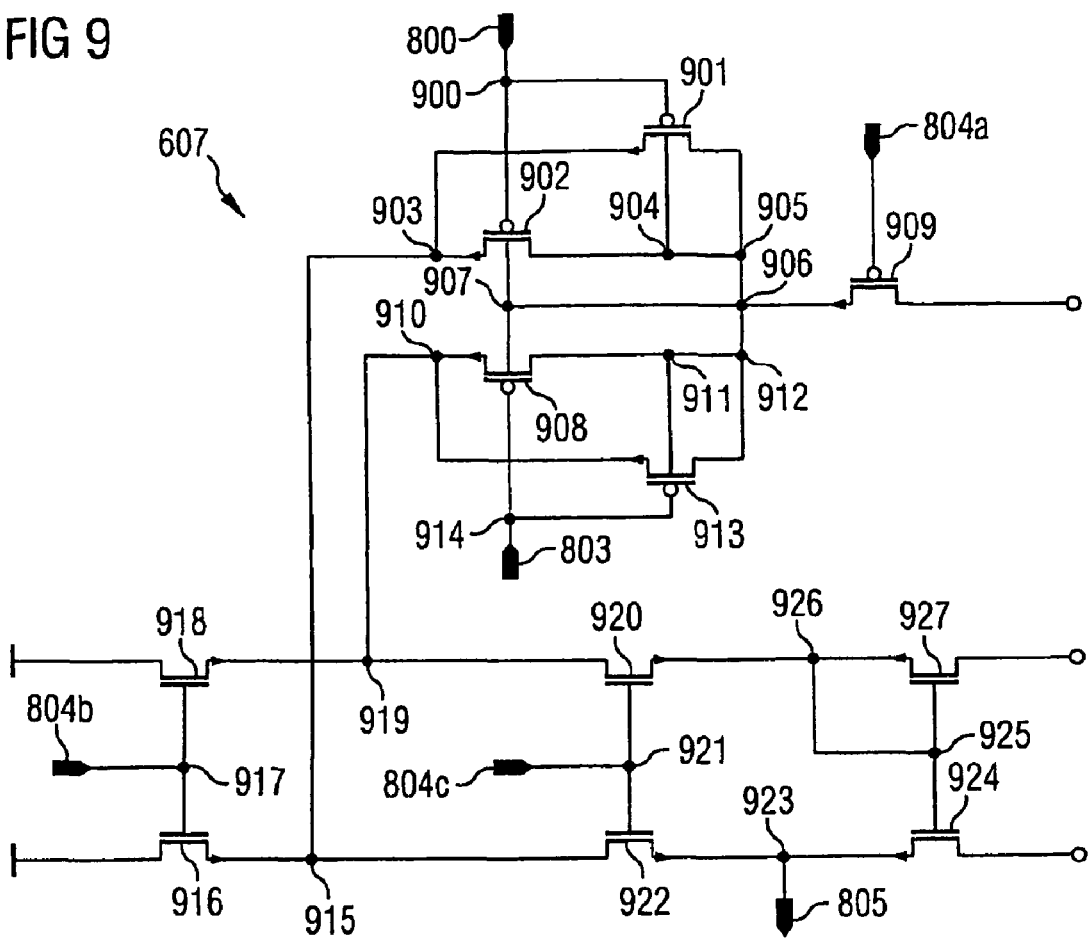
FIG. 9 shows a further block diagram showing the construction of the first comparator element shown in FIG. 8.

The noninverted input 800 of the operational amplifier 607 as shown in FIG. 9 is coupled to a first electrical node 900. The first electrical node 900 is coupled to the gate region of a first transistor 901. Furthermore, the first electrical node 900 is coupled to the gate region of a second transistor 902. One source/drain region of the first transistor 901 is coupled to a second electrical node 903.

The other source/drain region of the second transistor 902 is coupled to a third electrical node 904. The third electrical node 904 is coupled to the first transistor 901 and is identical to a fourth electrical node 905. The fourth electrical node 905 is coupled to the other source/drain region of the first transistor 901. Furthermore, the fourth electrical node 905 is identical to a fifth electrical node 906.

The fifth electrical node 906 is identical to a sixth electrical node 907. The sixth electrical node 907 is coupled both to the second transistor 902 and to a third transistor 908. The fifth electrical node 906 is furthermore coupled to one source/drain region of a fourth transistor 909. The gate region of the fourth transistor 909 is coupled to the first terminal 804a of the operational amplifier 607.

One source/drain region of the third transistor 908 is coupled to a seventh electrical node 910. The other source/drain region of the third transistor 908 is coupled to an eighth electrical node 911. The eighth electrical node 911 is identical to a ninth electrical node 912. The ninth electrical node 912 is coupled to one source/drain region of a fifth transistor 913. Furthermore, the ninth electrical node 912 is identical to the fifth electrical node 906.

The other source/drain region of the fifth transistor 913 is coupled to the seventh electrical node 910. Furthermore, the eighth electrical node 911 is coupled to the fifth transistor 913. The gate region of the third transistor 908 is coupled to a tenth electrical node 914. The tenth electrical node 914 is furthermore coupled to the gate region of the fifth transistor 913.

Furthermore, the tenth electrical node 914 is coupled to the inverted input 803 of the operational amplifier 607. The second electrical node 903 is identical to an eleventh electrical node 915. The eleventh electrical node 915 is coupled to one source/drain region of a sixth transistor 916. The gate region of the sixth transistor 916 is coupled to a twelfth electrical node 917.

The twelfth electrical node 917 is coupled to the second terminal 804b of the comparator unit 607. Furthermore, the twelfth electrical node 917 is coupled to the gate region of a seventh transistor 918. One source/drain region of the seventh transistor 918 is coupled to a thirteenth electrical node 919. The thirteenth electrical node 919 is identical to the seventh electrical node 910.

Furthermore, the thirteenth electrical node 919 is coupled to the first source/drain region of an eighth transistor 920. The gate region of the eighth transistor 920 is coupled to a fourteenth electrical node 921. The fourteenth electrical node 921 is coupled to the third terminal 804c of the operational amplifier 607 and is furthermore coupled to the gate region of a ninth transistor 922. One source/drain region of the ninth transistor 922 is coupled to the eleventh electrical node 915 and the other source/drain region of the ninth transistor 922 is coupled to a fifteenth electrical node 923.

The fifteenth electrical node 923 is coupled to the output 805 of the operational amplifier 607 and is furthermore coupled to one source/drain region of a tenth transistor 924. The gate region of the tenth transistor 924 is coupled to a sixteenth electrical node 925. The sixteenth electrical node 925 is furthermore identical to a seventeenth electrical node 926. The seventeenth electrical node 926 is coupled to one source/drain region of an eleventh transistor 927, and the gate region of the eleventh transistor 927 is coupled to the sixteenth electrical node 925. Furthermore, the seventeenth electrical node 926 is coupled to the other source/drain region of the eighth transistor 920.

An example embodiment of the second comparator element 610 shown in FIG. 6B, FIG. 7 is described below with reference to FIG. 10.

Figure 10:
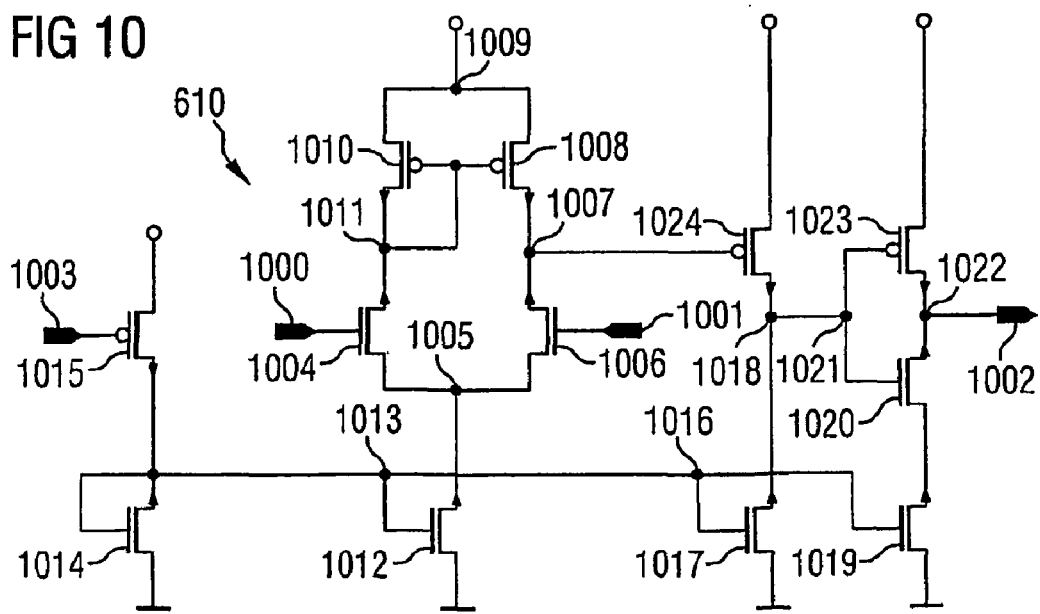
FIG. 10 shows a further block diagram showing the construction of a second comparator element shown in FIG. 7.

The comparator element 610 shown in FIG. 10 has a first input 1000 coupled to the seventh electrical node 713 shown in FIG. 7. The comparator element 610 furthermore has a second input 1001 coupled to the eighth electrical node 714 from FIG. 7. Furthermore, the comparator element 610 has an output 1002 coupled to the tenth electrical node 717 of the circuit arrangement 700 from FIG. 7. Furthermore, the second comparator element 610 has a supply input 1003, which is coupled to the fourteenth electrical node 725 of the circuit arrangement 700 and which is thus indirectly electrically coupled to the second voltage supply unit 724.

The first input 1000 is coupled to the gate region of a first transistor 1004. One source/drain region of the first transistor 1004 is coupled to a first electrical node 1005. The first electrical node 1005 is furthermore coupled to one source/drain region of a second transistor 1006. The gate region of the second transistor 1006 is coupled to the second input 1001 of the second comparator element 610.

The other source/drain region of the second transistor 1006 is coupled to a second electrical node 1007. The second electrical node 1007 is coupled to one source/drain region of a third transistor 1008. The other source/drain region of the third transistor 1008 is coupled to a third electrical node 1009. The third electrical node 1009 is coupled to one source/drain region of a fourth transistor 1010.

The gate region of the third transistor 1008 is coupled to the gate region of the fourth transistor 1010, and the gate region of the fourth transistor 1010 is furthermore coupled to a fourth electrical node 1011. The fourth electrical node 1011 is coupled to the other source/drain region of the first transistor 1004. Furthermore, the first electrical node 1005 is coupled to one source/drain region of a fifth transistor 1012.

The gate region of the fifth transistor 1012 is coupled to a fifth electrical node 1013. The fifth electrical node 1013 is coupled to the gate region and to one source/drain region of a sixth transistor 1014. One source/drain region of the sixth transistor 1014 is coupled to one source/drain region of a seventh transistor 1015. Furthermore, the gate region of the seventh transistor 1015 is coupled to the supply input 1003.

The fifth electrical node 1013 is identical to a sixth electrical node 1016. Furthermore, the sixth electrical node 1016 is coupled to the gate region of an eighth transistor 1017. One source/drain region of the eighth transistor 1017 is coupled to a seventh electrical node 1018. The sixth electrical node 1016 is furthermore coupled to the gate region of a ninth transistor 1019.

One source/drain region of the ninth transistor 1019 is coupled to one source/drain region of a tenth transistor 1020. The seventh electrical node 1018 is identical to an eighth electrical node 1021. The gate region of the tenth transistor 1020 is coupled to the eighth electrical node 1021. The other source/drain region of the tenth transistor 1020 is coupled to a ninth electrical node 1022. The ninth electrical node 1022 is coupled to the output 1002 of the second comparator element 610. Furthermore, the ninth electrical node 1022 is coupled to one source/drain region of an eleventh transistor 1023. The eighth electrical node 1021 is coupled to the gate region of the eleventh transistor 1023.

Furthermore, the seventh electrical node 1018 is coupled to one source/drain region of a twelfth transistor 1024. The gate region of the twelfth transistor 1024 is coupled to the second electrical node 1007.

An example embodiment of a counter element of the circuit arrangement according to the invention is described below with reference to FIG. 11.

Figure 11:
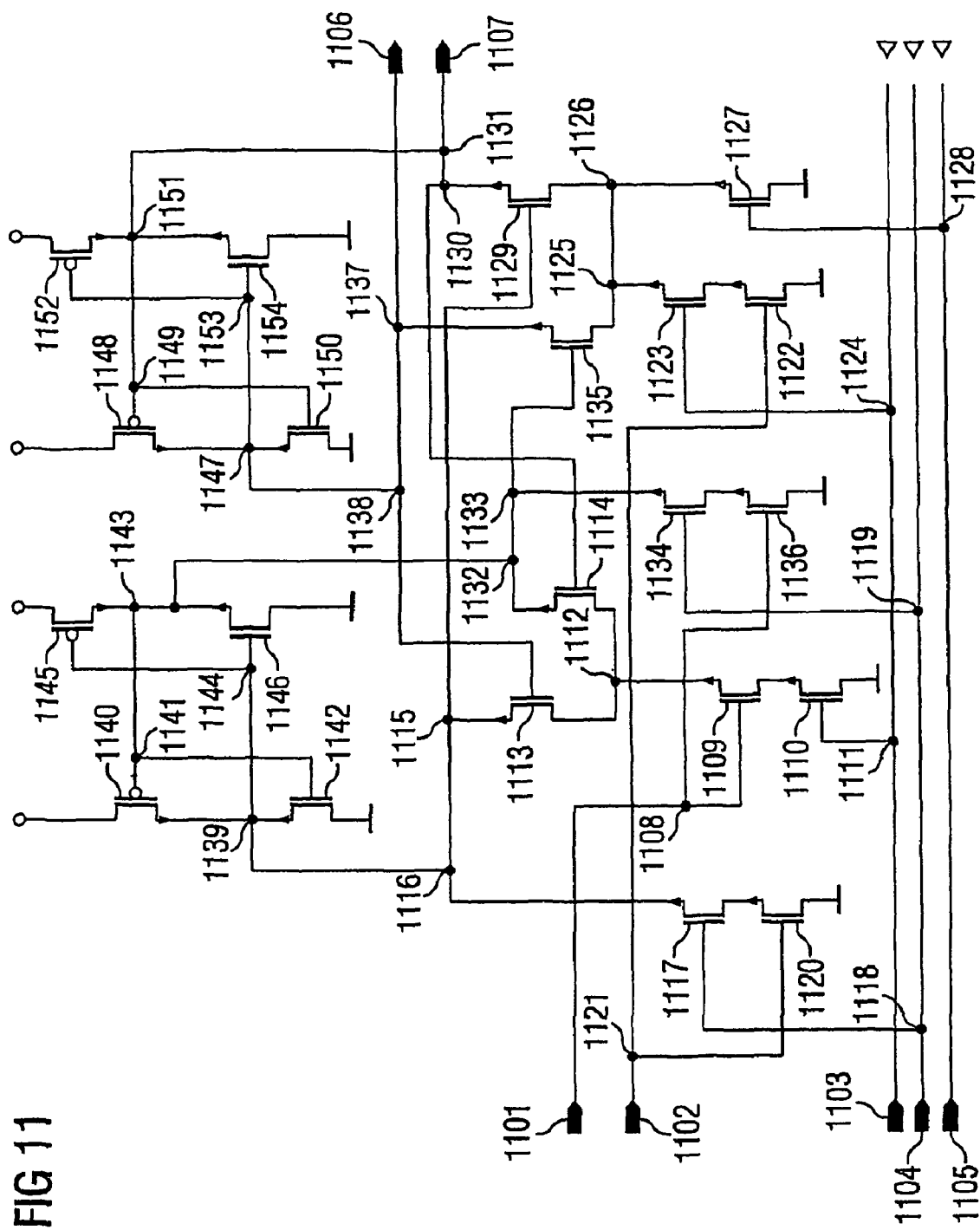
FIG. 11 shows a further block diagram showing the construction of a stage of the counter and of the shift register, respectively, from FIG. 7.

The counter element 1100 shown in FIG. 11 has a first input 1101, a second input 1102, a third input 1103, a fourth input 1104 and a fifth input 1105. Furthermore, the counter element 1100 has a first output 1106 and a second output 1107. The first input 1101 is coupled to a first electrical node 1108. The first electrical node 1108 is coupled to the gate region of a first transistor 1109.

One source/drain region of the first transistor 1109 is coupled to one source/drain region of a second transistor 1110. The gate region of the second transistor 1110 is coupled to a second electrical node 1111. The second electrical node 1111 is coupled to the third input 1103 of the counter element 1100.

The other source/drain region of the first transistor 1109 is coupled to a third electrical node 1112. The third electrical node 1112 is coupled to one source/drain region of a third transistor 1113. Furthermore, the third electrical node 1112 is coupled to one source/drain region of a fourth transistor 1114. The other source/drain region of the third transistor 1113 is coupled to a fourth electrical node 1115. The fourth electrical node 1115 is coupled to a fifth electrical node 1116. The fifth electrical node 1116 is coupled to one source/drain region of a fifth transistor 1117. The gate region of the fifth transistor 1117 is coupled to a sixth electrical node 1118.

The sixth electrical node 1118 is coupled to the fourth input 1104 of the counter element 1100. Furthermore, the sixth electrical node 1118 is identical to a seventh electrical node 1119. The other source/drain region of the fifth transistor 1117 is coupled to one source/drain region of a sixth transistor 1120. The gate region of the sixth transistor 1120 is coupled to an eighth electrical node 1121. The eighth electrical node 1121 is coupled to the second input 1102 of the counter element 1100.

Furthermore, the eighth electrical node 1121 is coupled to the gate region of a seventh transistor 1122. One source/drain region of the seventh transistor 1122 is coupled to one source/drain region of an eighth transistor 1123. The gate region of the eighth transistor 1123 is coupled to a ninth electrical node 1124.

The ninth electrical node 1124 is identical to the second electrical node 1111. The other source/drain region of the eighth transistor 1123 is coupled to a tenth electrical node 1125. The tenth electrical node 1125 is identical to an eleventh electrical node 1126. The eleventh electrical node 1126 is coupled to one source/drain region of a ninth transistor 1127. The gate region of the ninth transistor 1127 is coupled to a twelfth electrical node 1128. The twelfth electrical node 1128 is coupled to the fifth input 1105 of the counter element 1100.

The eleventh electrical node 1126 is coupled to one source/drain region of a tenth transistor 1129. The gate region of the tenth transistor 1129 is coupled to the fourth electrical node 1115. The other source/drain region of the tenth transistor 1129 is coupled to a thirteenth electrical node 1130. The thirteenth electrical node 1130 is identical to a fourteenth electrical node 1131. The fourteenth electrical node 1131 is coupled to the second output 1107 of the counter element 1100.

Furthermore, the thirteenth electrical node 1130 is coupled to the gate region of the fourth transistor 1114. The other source/drain region of the fourth transistor 1114 is coupled to a fifteenth electrical node 1132. The fifteenth electrical node 1132 is identical to a sixteenth electrical node 1133. The sixteenth electrical node 1133 is coupled to one source/drain region of an eleventh transistor 1134.

The sixteenth electrical node 1133 is furthermore coupled to the gate region of a twelfth transistor 1135. One source/drain region of the twelfth transistor 1135 is coupled to the tenth electrical node 1125. The gate region of the eleventh transistor 1134 is coupled to the seventh electrical node 1119. The other source/drain region of the eleventh transistor 1134 is coupled to one source/drain region of a thirteenth transistor 1136. The gate region of the thirteenth transistor 1136 is coupled to the first electrical node 1108.

The other source/drain region of the twelfth transistor 1135 is coupled to a seventeenth electrical node 1137. The seventeenth electrical node 1137 is identical to an eighteenth electrical node 1138. Furthermore, the seventeenth electrical node 1137 is coupled to the first output 1106 of the counter element 1100. The gate region of the third transistor 1113 is furthermore coupled to the eighteenth electrical node 1138. The fifth electrical node 1116 is identical to a nineteenth electrical node 1139. The nineteenth electrical node 1139 is coupled to one source/drain region of a fourteenth transistor 1140.

The gate region of the fourteenth transistor 1140 is coupled to a twentieth electrical node 1141. The twentieth electrical node 1140 is coupled to the gate region of a fifteenth transistor 1142. The nineteenth electrical node 1139 is coupled to one source/drain region of the fifteenth transistor 1142. The gate region of the fourteenth transistor 1140 is coupled to a twenty-first electrical node 1143.

A twenty-second electrical node 1144 is identical to the nineteenth electrical node 1139. The twenty-second electrical node 1143 is coupled to one source/drain region of a sixteenth transistor 1145. The gate region of the sixteenth transistor 1145 is coupled to the twenty-second electrical node 1144. The gate region of a seventeenth transistor 1146 is coupled to the twenty-second electrical node 1144.

One source/drain region of the seventeenth transistor 1146 is coupled to the twenty-first electrical node 1143. The twenty-second electrical node 1143 is identical to the fifteenth electrical node 1132. Furthermore, the twenty-second electrical node 1144 is coupled to the gate region of a seventeenth transistor 1146, one source/drain region of the seventeenth transistor 1146 being coupled to the twenty-first electrical node 1143.

The nineteenth electrical node 1138 is identical to a twenty-third electrical node 1147. The twenty-third electrical node 1147 is coupled to one source/drain region of an eighteenth transistor 1148. The gate region of the eighteenth transistor 1148 is coupled to a twenty-fourth electrical node 1149.

The twenty-fourth electrical node 1149 is coupled to the gate region of a nineteenth transistor 1150. The twenty-third electrical node 1147 is coupled to one source/drain region of the nineteenth transistor 1150. The gate region of the eighteenth transistor 1148 is coupled to a twenty-fifth electrical node 1151. The twenty-fifth electrical node 1151 is coupled to one source/drain region of a twentieth transistor 1152.

The gate region of the twentieth transistor 1152 is coupled to a twenty-sixth electrical node 1153. The twenty-sixth electrical node 1153 is identical to the twenty-third electrical node 1147.

The twenty-fifth electrical node 1151 is coupled to one source/drain region of a twenty-first transistor 1154. The gate region of the twenty-first transistor 1154 is coupled to the twenty-sixth electrical node 1153. The twenty-fifth electrical node 1151 is identical to the fourteenth electrical node 1131. The first electrical node 1108 is coupled to the gate region of the thirteenth transistor 1136.

FIG. 12 shows an example embodiment of the sensor arrangement 1200 according to the invention having a plurality of circuit arrangements 1201 (each of which may be configured like the circuit arrangement 700 shown in FIG. 7) arranged in matrix form on a chip 1202. Each of the circuit arrangements 1200 may be operated as a sensor independently of the other circuit arrangements.

If the circuit arrangements 1200 are configured as sensors for detecting different molecules (e.g. each has capture molecules that can be hybridized with a specific type of DNA strands), then a parallel analysis of a liquid to be investigated is possible by use of the sensor arrangement 1200. In this case, circuit units that serve for driving, for voltage and current supply and for read-out of the sensor cells are situated at the edge of the matrix-type arrangement of sensor electrodes.

These circuit units supply for example the reference current 621a for calibrating the individual sensor arrays, supply and reference voltages for the control unit 602 and comparator unit 603 contained in the sensor elements, and also the digital control signals for the counter 736. These are, in particular, a reset signal for the counter, a changeover signal for the counter/shift register operation, and also, if appropriate, a changeover signal for further capacitors connected in parallel with the first capacitor 604.

In particular, the units at the edge of the matrix contain the circuits for preevaluation of the measured signals, in particular for read-out, storage and further processing of the counter contents of the individual sensor elements.

The advantages of the sensor circuit according to at least one embodiment of the invention are particularly manifested in an arrangement of a multiplicity of sensor units on a semiconductor chip since each sensor element is able autonomously to measure the current signal of the sensor electrodes and to store it in the form of a digital counter signal within the sensor element. At the same time, the electrode potential is held constant at the desired potential. Said counter signal can then be interrogated and processed further at an arbitrary point in time by means of the circuit units at the edge of the matrix.

On account of the high word width of the binary counter 736, it is expedient to serially read out the counter reading from the sensor elements since, in the case of a parallel read-out, very wide data buses would have to be routed over the entire matrix. The serial outputting of the counter reading is effected by changing over the binary counter 736 from the counter operating mode to the shift register operating mode.

By the application of a clock signal, the counter content, that is to say the individual data bits in the counter stages, is then progressively advanced into the respectively downstream counter stage, so that all the data bits of an n-stage counter are output at the output of the counter after n clock pulses. The number of required counter stages is associated directly with the required dynamic range.

By way of example, if the intention is to register a measurement signal with an accuracy of 6 bits in a measurement range of 5 decades, a counter having a word width of 23 bits is necessary. The use of serial protocols for data communication is advantageous in particular also because this simultaneously simplifies communication with the read-out device into which the chip is inserted.

The use of a counter circuit within the sensor unit is not absolutely necessary. Instead of using this, it is also possible, by way of example, to directly output the output signal of the pulse transmitter 613 in which the measured current intensity at the sensor electrodes is coded in the form of a frequency. The circuit units at the edge of the matrix then serve for measuring and further processing the frequencies or pulse durations of the individual sensor units.

FIG. 13 shows a circuit arrangement 1300 in accordance with the above exemplary embodiment in an overall illustration.

As illustrated in FIG. 13, an electrochemical system 1301 has an analyte, which may contain the macromolecular biopolymers to be registered. Furthermore, a generator electrode 1302 is provided, which is set up together with a collector electrode 1303 as an interdigital electrode. Furthermore, a reference electrode 1304 and a counterelectrode 1305 are provided for setting the desired electrical potential in the analyte.

The reference electrode 1304 is coupled to the inverting input 1306 of a reference potential setting operational amplifier 1307, the noninverting input 1308 of which is coupled to the ground potential via a reference potential voltage source 1309. The output 1310 of the reference potential setting operational amplifier 1307 is coupled to the counterelectrode 1305. Consequently, the electrochemical system 1301 has four electrodes 1302, 1303, 1304 and 1305 which are electrochemically coupled by way of the analyte.

The potentiostat formed by the reference potential setting operational amplifier 1307 measures the electrochemical potential by way of the reference electrode 1304 and the electrochemical potential is readjusted, by means of the counterelectrode 1305, to the predetermined desired value that is predetermined by way of the reference potential voltage source 1309.

For correct functioning of the circuits, the desired value should lie between the positive and the negative operating voltage of the circuit. The value of the reference potential typically lies in the middle between the positive operating voltage $V_{DD}$ and the negative operating voltage $V_{SS}$ of the circuit. However, it should be noted that the absolute value is not critical in this case since only the voltage differences between the electrodes 1302, 1303, 1304 and 1305 are of importance for the electrochemical system 1301. The potentiostat circuit formed by the reference potential setting operational amplifier 1307 is present only once on the entire sensor chip and is not explained in any further detail below.

Furthermore, FIG. 13 shows a generator comparator element 1311, which forms the first circuit unit and the inverting input 1312 of which is coupled to the generator electrode 1302 and the noninverting input 1313 of which is coupled to the ground potential via a first reference voltage source 1314, so that the generator desired potential $AGND_{+V\_ox}$ is adjusted by way of the generator comparator element 1311, which is formed by an opposite operational amplifier and constitutes a control amplifier. An output 1315 of the generator comparator element 1311 is coupled to a gate terminal of a first NMOS transistor 1316, the first source/drain region of which is coupled to the generator electrode 1302 and the inverting input 1312 of the generator comparator element 1311 and the second source/drain region of which is coupled to a first terminal of a first capacitor 1317, the second terminal of which is coupled to the positive operating potential $V_{DD}$ 1318.

The first terminal of the first capacitor 1317 is furthermore coupled to a first node K1 1319, which is in turn coupled to an inverting input 1320 of a second generator comparator element 1321, the noninverting input 1322 of which is coupled to the ground potential via a second reference voltage source 1323 that defines a second generator desired potential. An output 1324 of the second generator comparator element 1321, which is likewise formed by an operational amplifier, is coupled to an input of a pulse generator 1325, which, on the output side, closes a first switch S1 1326 as long as the pulse generator 1325 generates a pulse. The first switch S1 1326 has a first terminal coupled to the first node K1 1319, and a second terminal coupled to the positive operating potential $V_{DD}$ 1318.

Clearly, the first node K1 1319 is thus coupled to the positive operating potential $V_{DD}$ when the first switch S1 1326 is closed. Furthermore, the output of the first pulse generator 1325 is coupled to a first counter element 1327, which can be switched into a shift register mode and provides first result data Data1 on the output side.

Furthermore, an inverting input 1328 of a collector comparator element 1329 is coupled to the collector electrode 1303. The noninverting input 1330 of the collector comparator element 1329 formed as an operational amplifier is coupled to the ground potential via a third reference voltage source 1331. The output 1332 of the collector comparator element 1329 is coupled to a gate terminal of a first PMOS transistor 1333, the first source/drain region of which is coupled to the collector electrode 1303 and the second source/drain region of which is coupled to a third node K3 1334.

The second potentiostat circuit described above serves for adjusting the potential at the collector electrode 1303 to the desired potential $AGND_{+V\_red}$ defined by way of the third reference voltage source 1331.

Furthermore, a first terminal of a third capacitor 1335 is coupled to the third node K3 1334, the second terminal of said third capacitor being coupled to the negative operating potential $V_{SS}$ 1336.

Furthermore, the third node K3 1334 is coupled to the inverting input 1337 of a second collector comparator element 1338, the noninverting input 1339 of which is connected to the ground potential via a fourth reference voltage source 1340.

An output 1341 of the second collector comparator element 1338 is coupled to an input of a second pulse generator 1342, the output of which is fed back to a third switch S3 1343 and closes this switch as long as a pulse is generated. A first terminal of the third switch S3 1343 is coupled to the negative operating potential $V_{SS}$ 1336 and furthermore to the second terminal of the third capacitor 1335, and a second terminal of the third switch S3 1343 is coupled to the third node K3 1334.

Consequently, the third node K3 1334 is coupled to the negative operating potential $V_{SS}$ 1336 via the third switch S3 1343 when the switch is closed. Furthermore, the output of the second pulse generator 1342 is coupled to a second counter element 1344, which is likewise equipped with a shift register mode and provides second result data Data2 on the output side.

Clearly, in the case of the circuit arrangement described above, the voltages at the sensor electrodes are adjusted relative to the voltage AGND by way of the control amplifiers 1331 and 1329, that is to say by means of the first generator comparator element 1311 and the first collector comparator element 1329, to be precise the potential at the generator electrode 1302 to the potential $AGND_{+V\_ox}$ of the first reference voltage source 1314 and the potential of the collector electrode 1303 to the third reference voltage $AGND_{+V\_red}$, where V_ox is the oxidation potential and V_red is the reduction potential of the electrochemical species involved in the redox cycling.

The analog/digital conversion is effected independently for the two electrodes 1302, 1303 with the aid of a respective sawtooth generator, that is to say via the pulse generators 1325, 1342.

In this case, the current derived from the sensor is drawn from the respective capacitor 1317, 1335. The respective capacitor is discharged as a result of this. The voltage at the capacitors is monitored by use of two comparators. If the voltage reaches a predetermined value, then the comparators trigger a reset pulse. By this pulse, the respective capacitor is recharged again. The number of reset pulses per unit time is a measure of the current of the sensor. The two subcircuits at the two electrodes are designed complementarily with respect to one another in this case; the circuit for the generator electrode (upper half) operates as a current source and the circuit for the collector electrode 1303 (lower half) operates as a current sink. Moreover, the two subcircuits operate independently of one another.

Since the currents in the generator electrode 1302 and in the collector electrode 1303 essentially carry the same information, it is possible to measure only the sum in terms of absolute value of the two signals.

A suitable circuit for measuring the sum in terms of absolute value of the two current signals is shown in FIG. 14.

Identical components in the circuit arrangements 1300 and 1400 are provided with identical reference symbols.

The circuit arrangement 1400 in accordance with the second example embodiment of the invention has one comparator and one counter element fewer than the circuit arrangement 1300 in accordance with the first example embodiment of the invention.

In contrast to the circuit arrangement 1300 described above, the circuit arrangement 1400 in accordance with the second example embodiment of the invention has a different second and fourth circuit unit.

The electrochemical system itself and the first circuit unit and the third circuit unit remain unchanged.

In the case of the circuit arrangement 1400, the first node K1 1319 is coupled to a second capacitor 1401, the second terminal of which is connected in series with the first capacitor, which first capacitor 1317 is coupled to the positive operating potential $V_{DD}$ 1318 by its second terminal.

The first capacitor 1317 and the second capacitor 1401 form a first capacitive voltage divider 1402.

The second terminal of the second capacitor 1401 and the first terminal of the first capacitor 1317 are furthermore coupled to a second node K2 1403, which is in turn coupled to the noninverting input 1404 of a summation comparator element 1405. Furthermore, the second node K2 1403 is coupled to a first terminal of the first switch S1 1326, the second terminal of which is coupled to the second reference voltage source 1323 and, via the latter, to the ground potential, so that, for the case where the first switch S1 1326 is closed, the second node K2 1403 is at the second reference voltage VREF1. The first switch S1 1326 is closed as long as the summation pulse generator 1413 generates a pulse. In the same way, the summation pulse generator 1413 closes a second switch S2 1406, which, in the closed state, couples the first node K1 1319 to the positive operating potential $V_{DD}$ 1318.

Furthermore, the third node K3 1334 is coupled to a fourth capacitor 1407, the second terminal of which is coupled to the first terminal of the third capacitor 1335, the second terminal of which is coupled to the negative operating potential $V_{SS}$ 1336.

The third capacitor 1335 and the fourth capacitor 1407 are thus likewise connected in series and form a second capacitive voltage divider 1408.

The second terminal of the fourth capacitor 1407 and the first terminal of the third capacitor 1335 are coupled to a fourth node K4 1409, which is in turn coupled to the inverting input 1410 of the summation comparator element 1405. Furthermore, the fourth node K4 1409 is coupled to the third switch S3 1343, which, in the closed switch position, connects the fourth reference voltage source 1340 to the fourth node K4 1409, which in this case has the fourth reference potential VREF2. The third switch S3 1343 is closed as long as the summation pulse generator 1413 generates a pulse.

In the same way, the summation pulse generator 1413 closes a fourth switch S4 1411. This fourth switch S4 1411, in the closed switch position, couples the negative operating potential $V_{SS}$ 1336 to the third node K3 1334, so that the negative operating potential $V_{SS}$ 1336 is present at the latter.

The output 1412 of the summation comparator element 1405 is coupled to a summation pulse generator 1413, which, on the output side, is coupled on the one hand to the first switch S1 1326 and the second switch S2 1406 and on the other hand to the third switch S3 1343 and the fourth switch S4 1411 and controls them. Furthermore, the output of the summation pulse generator 1413 is coupled to a summation counter element 1414, which is likewise configured with a shift register mode and, on the output side, provides the result data Data of the sensor method.

It should be noted in this context that the capacitance of the second capacitor is chosen to be significantly greater than that of the first capacitor, preferably at least twice as large, particularly preferably greater by a factor of ten. The capacitance of the fourth capacitor 1407 is correspondingly chosen to be significantly greater than the capacitance of the third capacitor 1335, once again preferably at least twice as large, particularly preferably greater by a factor of ten.

The functioning of the circuit arrangement 1400 is very similar to the functioning of the circuit arrangement 1300 in accordance with the first example embodiment of the invention.

In accordance with this example embodiment of the invention, the current for the generator electrode 1302 is drawn from the first capacitive voltage divider 1402. Since the capacitance of the second capacitor 1401 is significantly greater than the capacitance of the first capacitor 1317, the first node K1 1319 and the second node K2 1403 are strongly coupled to one another and the voltage swing is essentially identical on both nodes. The same applies correspondingly on the collector side.

Since the capacitance of the fourth capacitor 1407 is chosen to be significantly greater than the capacitance of the third capacitor 1335, the voltage swing is transferred from the third node K3 1334 virtually completely to the fourth node K4 1409. The second node K2 1403 and the fourth node K4 1409 have oppositely directed signals which are compared with one another in the summation comparator element 1405.

Downstream pulse shaping by way of the summation pulse generator 1413 in turn provides for a well-shaped reset pulse.

All of the switches S1 to S4 are closed during the reset pulse. The first node K1 1319 is thus reset to the positive operating potential $V_{DD}$ 1318, the third node K3 1334 is reset to the negative operating potential $V_{SS}$ 1336, the second node K2 1403 is reset to the third reference potential VREF1 and the fourth node K4 1409 is reset to the fourth reference potential VREF2. In this case, the third reference potential and the fourth reference potential are chosen such that the summation comparator element 1405 is operated in a favorable operating range.

FIG. 15b shows a simulation of the time profile of the voltages at the four nodes K1 to K4,
- a first voltage profile 1501 showing the voltage profile at the first node K1 1319,
- a second voltage profile 1502 showing the voltage profile at the second node K2 1403,
- a third voltage profile 1503 showing the voltage profile at the third node K3 1334, and
- a fourth voltage profile 1504 showing the voltage profile at the fourth node K4 1409.

Furthermore, FIG. 15a illustrates corresponding reset pulses 1505, that is to say the voltage profile at a fifth node K5 1415, the output of the summation pulse generator 1413.

The following simulation parameters were used for determining the simulation result illustrated in FIG. 15a and FIG. 15b:
- electrode current: 1 nA,
- capacitance of the first capacitor=100 fF,
- capacitance of the third capacitor=100 fF,
- capacitance of second capacitor=1 pF,
- capacitance of fourth capacitor=1 pF,
- positive operating voltage $V_{DD}$=5 V,
- AGND=2.5 V,
- V_ox=0.1 V,
- V_red=0.1 V,
- VREF1=2.5 V,
- VREF2=1.5 V.

The simulation was effected using nominal parameters for a circuit in a 0.5 μm-5 V standard CMOS process.

In an alternative configuration of the circuit arrangement 1400, provision is made for measuring either only the collector current or only the generator current. For the purpose of measuring the collector current, by way of example, the first switch S1 1326 and the second switch S2 1406 are permanently closed. In this way, the controller for the generator voltage, that is to say the first generator comparator element 1311, is permanently connected to the positive operating potential VDD 1318 and the noninverting comparator input of the summation comparator element 1405 (1404) is at the third reference potential VREF1. The potential at the fourth node K4 1409 thus rises until the third reference potential VREF1 has been reached, and is then reset to the fourth reference potential VREF2 by means of the reset pulse.

Correspondingly, the third switch S3 1343 and the fourth switch S4 1410 may also be permanently closed. In this case, only the generator current is measured. The measurement of only one current may be a good test possibility for monitoring the symmetry of the electrochemical signals.

Figure 16:
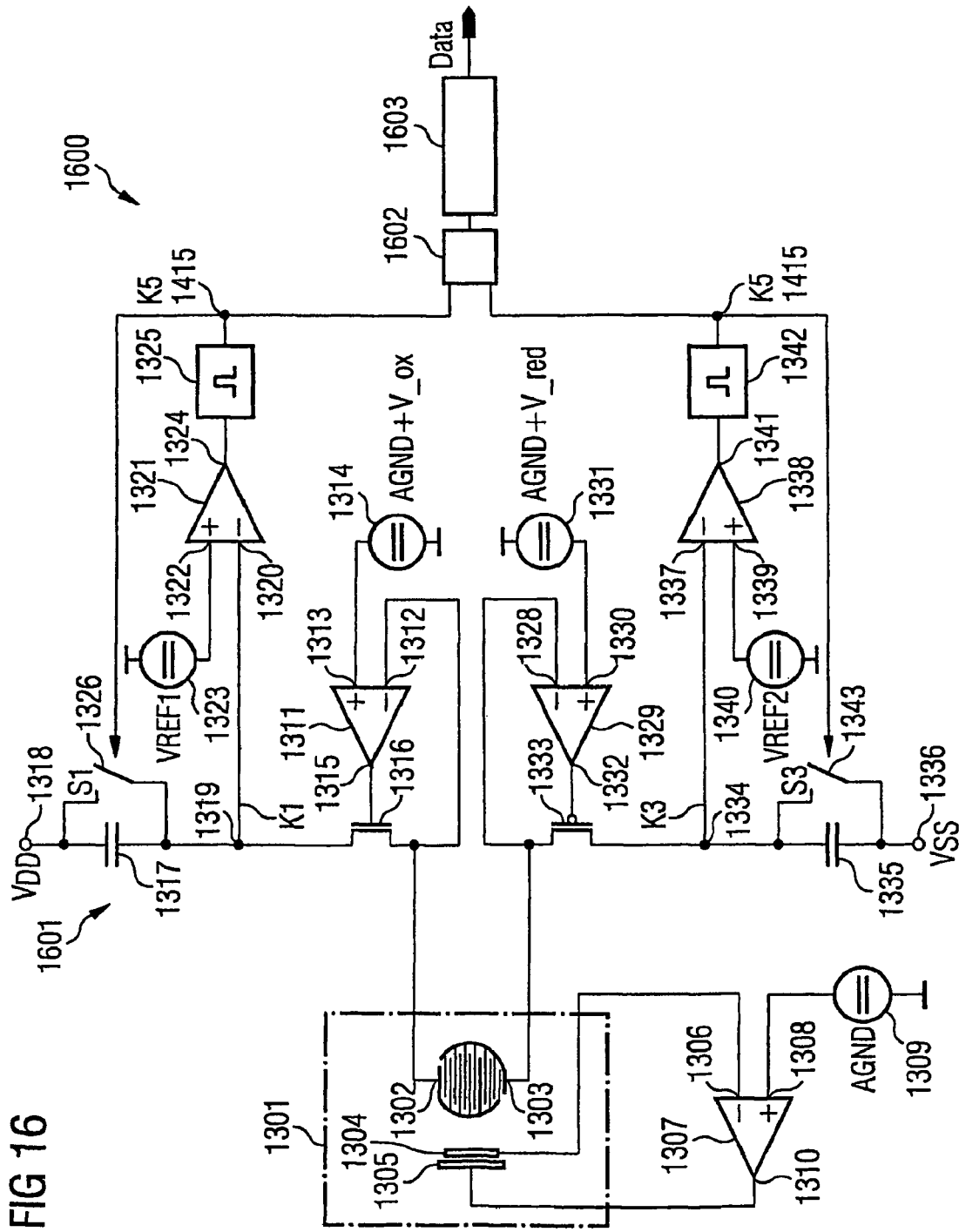
FIG. 16 shows a circuit arrangement in accordance with a third example embodiment of the invention.

FIG. 16 shows a circuit arrangement 1600 in accordance with a third example embodiment of the invention. In this figure, identical electrical components of the circuit arrangement 1600 in accordance with the third example embodiment and the circuit arrangement 1300 in accordance with the first example embodiment of the invention are provided with identical reference symbols. In the case of the circuit arrangement 1600, the entire analog side 1601 is configured in the same way as in the case of the circuit arrangement 1300 in accordance with the first example embodiment of the invention.

In accordance with this example embodiment, however, one of the two counter elements 1327 and 1344 provided in the circuit arrangement 1300 is saved by virtue of the two pulse sequences generated by the first pulse generator 1325 and the second pulse generator 1342 being processed by way of just one summation counter element 1603.

According to at least one embodiment of the invention, in this case provision is made of just a simple digital circuit, preferably set up as a buffer circuit, generally referred to as a synchronization element 1602, which, even in the case where the two pulse sequences generated overlap temporally, outputs in controlled fashion two pulses that are output temporally successively.

In this case, too, it is possible of course, as in the case of the above-described circuit arrangement 1400 in accordance with the second example embodiment of the invention, for test purposes to count only one pulse sequence and to block the other pulse sequence.

The following publications are cited in this document:

[1] Hintsche, R., Paeschke, M., Uhlig, A., Seitz, R. (1997) "Microbiosensors using Electrodes made in Si-technology", Frontiers in Biosensorics, Fundamental Aspects, Scheller, F W., Schubert, F., Fedrowitz, J. (eds.), Birkhauser Verlag Basle, Switzerland, pp. 267-283

[2] van Gerwen, P. (1997) "Nanoscaled Interdigitated Electrode Arrays for Biochemical Sensors", IEEE, International Conference on Solid-State Sensors and Actuators, Jun. 16-19, 1997, Chicago, pp. 907-910

[3] Paeschke, M., Dietrich, F., Uhlig, A., Hintsche, R. (1996) "Voltammetric Multichannel Measurements Using Silicon Fabricated Microelectrode Arrays", Electroanalysis, Vol. 7, No. 1, pp. 1-8

[4] Uster, M., Loeliger, T., Guggenbühl, W., Jäckel, H. (1999) "Integrating ADC Using a Single Transistor as Integrator and Amplifier for Very Low (1fA Minimum) Input Currents", Advanced A/D and D/A Conversion Techniques and Their Applications, Conference at the University of Strathclyde (Great Britain) Jul. 27-28, 1999, Conference Publication No. 466, pp. 86-89, IEE

[5] Breten, M., Lehmann, T., Bruun, E. (2000) "Integrating data converter for picoampere currents from electrochemical transducers", ISACS 2000, IEEE International Symposium on Circuits and Systems, May 28-31, 2000, Geneva, Switzerland

[6] U.S. Pat. No. 3,711,779

[7] U.S. Pat. No. 4,199,728

LIST OF REFERENCE SYMBOLS

100 Circuit arrangement
101 Sensor electrode
102 First circuit unit
103 Second circuit unit
104 First capacitor
105 Capture molecules
106 Molecule to be registered
107 Enzyme label
108 Electrically charged particles
109 First control unit
110 Controllable nonreactive resistor
111 Second control unit
112 Pulse
113 Further switch
114 Voltage source
200 Sensor
201 Electrode
202 Electrode
203 Insulator
204 Electrode terminal
205 Electrode terminal 206 DNA probe molecule
207 Electrolyte
208 DNA strands
300 Interdigital electrode
400 Biosensor
401 First electrode
402 Second electrode
403 Insulator layer
404 Holding region of first electrode
405 DNA probe molecule
406 Electrolyte
407 DNA strand
408 Enzyme
409 Cleavable molecule
410 Negatively charged first partial molecule
411 Arrow
412 Further solution
413 Oxidized first partial molecule
414 Reduced first partial molecule
500 Diagram
501 Electric current
502 Time
503 Current-time curve profile
504 Offset current
600 Circuit arrangement
601 Sensor electrode
602 First circuit unit
603 Second circuit unit
604 First capacitor
605 Node
606 Counter element
607 First comparator element
608 Second voltage source
609 Transistor
610 Second comparator element
611 Third voltage source
612 Switch
613 Pulse transmitter
620 Circuit arrangement
621 Calibration device
621a Reference current source
622 Further switch
700 Circuit arrangement
701 Further sensor electrode
702 First electrical node
703 First transistor
704 Second electrical node
705 First voltage supply
706 Third electrical node
707 Fourth electrical node
708 First capacitance
709 Fifth electrical node
710 Sixth electrical node
711 Second capacitance
712 Second voltage supply
713 Seventh electrical node
714 Eighth electrical node
715 Third capacitance
716 Ninth electrical node
717 Tenth electrical node
718 Eleventh electrical node
719 Twelfth electrical node
720 Thirteenth electrical node
721 Fourth capacitance
722 Fifth capacitance
723 First voltage supply unit
724 Second voltage supply unit
725 Fourteenth electrical node
726 Fifteenth electrical node
727 Third voltage supply
728 Fourth voltage supply
729 First control signal
730 Second control signal
731 Third control signal
732 Fourth control signal
733 Fifth control signal
734 Sixth control signal
735 Seventh control signal
736 Counter unit
737 Sixteenth electrical node
738 Seventeenth electrical node
739 Eighteenth electrical node
740 Nineteenth electrical node
741 Twentieth electrical node
742 Twenty-first electrical node
743 Twenty-second electrical node
744 Sixth capacitance
745 Twenty-third electrical node
746 Seventh capacitance
747 Twenty-fourth electrical node
748 Output terminal
800 Noninverted input
801 First electrical node
802 Inverted input
803 First terminal
804a Second terminal
804b Third terminal
804c Output
806 Second electrical node
807 Capacitor
808 Third electrical node
810 Output terminal
900 First electrical node
901 First transistor
902 Second transistor
903 Second electrical node
904 Third electrical node
905 Fourth electrical node
906 Fifth electrical node
907 Sixth electrical node
908 Third transistor
909 Fourth transistor
910 Seventh electrical node
911 Eighth electrical node
912 Ninth electrical node
913 Fifth transistor
914 Tenth electrical node
915 Eleventh electrical node
916 Sixth transistor
917 Twelfth electrical node
918 Seventh transistor
919 Thirteenth electrical node
920 Eighth transistor
921 Fourteenth electrical node
922 Ninth transistor
923 Fifteenth electrical node
924 Tenth transistor
925 Sixteenth electrical node
926 Seventeenth electrical node
927 Eleventh transistor
1000 First input
1001 Second input
1002 Output
1003 Supply input 1004 First transistor
1005 First electrical node
1006 Second transistor
1007 Second electrical node
1008 Third transistor
1009 Third electrical node
1110 Fourth transistor
1111 Fourth electrical node
1112 Fifth transistor
1113 Fifth electrical node
1114 Sixth transistor
1115 Seventh transistor
1116 Sixth electrical node
1117 Eighth transistor
1118 Seventh electrical node
1119 Ninth transistor
1120 Tenth transistor
1121 Eighth electrical node
1122 Ninth electrical node
1123 Eleventh transistor
1124 Twelfth transistor
1100 Counter element
1101 First input
1102 Second input
1103 Third input
1104 Fourth input
1105 Fifth input
1106 First output
1107 Second output
1108 First electrical node
1109 First transistor
1110 Second transistor
1111 Second electrical node
1112 Third electrical node
1113 Third transistor
1114 Fourth transistor
1115 Fourth electrical node
1116 Fifth electrical node
1117 Fifth transistor
1118 Sixth electrical node
1119 Seventh electrical node
1120 Sixth transistor
1121 Eighth electrical node
1122 Seventh transistor
1123 Eighth transistor
1124 Ninth electrical node
1125 Tenth electrical node
1126 Eleventh electrical node
1127 Ninth transistor
1128 Twelfth electrical node
1129 Tenth transistor
1130 Thirteenth electrical node
1131 Fourteenth electrical node
1132 Fifteenth electrical node
1133 Sixteenth electrical node
1134 Eleventh transistor
1135 Twelfth transistor
1136 Thirteenth transistor
1137 Seventeenth electrical node
1138 Eighteenth electrical node
1139 Nineteenth electrical node
1140 Fourteenth transistor
1141 Twentieth electrical node
1142 Fifteenth transistor
1143 Twenty-first electrical node
1144 Twenty-second electrical node
1145 Sixteenth transistor
1146 Seventeenth transistor
1147 Twenty-third electrical node
1148 Eighteenth transistor
1149 Twenty-fourth electrical node
1150 Nineteenth transistor
1151 Twenty-fifth electrical node
1152 Twentieth transistor
1153 Twenty-sixth electrical node
1154 Twenty-first transistor
1200 Sensor arrangement
1201 Circuit arrangement
1202 Chip
1300 Circuit arrangement
1301 Electrochemical system
1302 Generator electrode
1303 Collector electrode
1304 Reference electrode
1305 Counterelectrode
1306 Inverting input of reference potential setting operational amplifier
1307 Reference potential setting operational amplifier
1308 Noninverting input of reference potential setting operational amplifier
1309 Analyte reference potential voltage source
1310 Output of reference potential setting operational amplifier
1311 First generator comparator element
1312 Inverting input of first generator comparator element
1313 Noninverting input of first generator comparator element
1314 First reference voltage source
1315 Output of first generator comparator element
1316 First NMOS transistor
1317 First capacitor
1318 Positive operating potential
1319 First node
1320 Inverting input of second generator comparator element
1321 Second generator comparator element
1322 Noninverting input of second generator comparator element
1323 Second reference voltage source
1324 Output of second generator comparator element
1325 First pulse generator
1326 First switch
1327 First counter element
1328 Inverting input of collector comparator element
1329 Collector comparator element
1330 Noninverting input of collector comparator element
1331 Third reference voltage source
1332 Output of collector comparator element
1333 First PMOS transistor
1334 Third node
1335 Third capacitor
1336 Negative operating potential
1337 Inverting input of second collector comparator element
1338 Second collector comparator element
1339 Noninverting input of second collector comparator element
1340 Fourth reference voltage source
1341 Output of second collector comparator element
1342 Second pulse generator
1343 Third switch
1344 Second counter element
1400 Circuit arrangement
1401 Second capacitor
1402 First capacitive voltage divider
1403 Second node 1404 Noninverting input of summation comparator element
1405 Summation comparator element
1406 Second switch
1407 Fourth capacitor
1408 Second capacitive voltage divider
1409 Fourth node
1410 Inverting input of summation comparator element
1411 Fourth switch
1412 Output of summation comparator element
1413 Summation pulse generator
1414 Summation counter element
1415 Fifth node
1501 First voltage profile
1502 Second voltage profile
1503 Third voltage profile
1504 Fourth voltage profile
1505 Reset pulse signal
1600 Circuit arrangement
1601 Analog side
1602 Synchronization element
1603 Summation counter element Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A circuit arrangement, comprising:
a sensor electrode;
a first circuit unit, electrically coupled to the sensor electrode;
a second circuit unit, including a first capacitor,
the first circuit unit configured to hold the electrical potential of the sensor electrode in a first reference range around an electrical first desired potential by coupling the first capacitor and the sensor electrode such that the electrical potential of the sensor electrode is matchable,
the sensor electrode configured to be a generator electrode,
the second circuit unit is configured to,
detect if the electrical potential of the first capacitor is outside a second reference range; and
bring the first capacitor to a first electrical potential;
a collector electrode;
a third circuit unit, electrically coupled to the collector electrode; and
a fourth circuit unit, including a second capacitor, the third circuit unit configured to hold the electrical potential of the collector electrode in a second reference range around an electrical second desired potential by coupling the second capacitor and the collector electrode such that the electrical potential of the collector electrode is matchable,
the second circuit unit and the fourth circuit unit configured to detect if the potential of the second capacitor is outside a second reference range and configured to bring the second capacitor to a second electrical reference potential.

2. The circuit arrangement as claimed in claim 1, further comprising:
a third capacitor coupled to the first capacitor, the third capacitor having a greater capacitance than the first capacitor and the first capacitor and the third capacitor forming a capacitive first voltage divider;
a fourth capacitor coupled to the second capacitor, the fourth capacitor having a greater capacitance than the second capacitor and the second capacitor and the fourth capacitor forming a capacitive second voltage divider.

3. The circuit arrangement as claimed in claim 2, wherein
the capacitance of the third capacitor is greater than the capacitance of the first capacitor at least by a factor of two; and
the capacitance of the fourth capacitor is greater than the capacitance of the second capacitor at least by a factor of two.

4. The circuit arrangement as claimed in claim 3, wherein the second circuit unit and the fourth circuit unit jointly have a summation comparator element having two inputs and an output,
a first input being connected between the first capacitor and the third capacitor,
a second input being connected between the second capacitor and the fourth capacitor, and
the output being coupled to a counter element such that the output counts at least one of the number and the temporal sequence of the events.

5. The circuit arrangement as claimed in claim 2, wherein the second circuit unit and the fourth circuit unit jointly have a summation comparator element having two inputs and an output,
a first input being connected between the first capacitor and the third capacitor,
a second input being connected between the second capacitor and the fourth capacitor, and
the output being coupled to a counter element such that the output counts at least one of the number and the temporal sequence of the events.

6. The circuit arrangement as claimed in claim 1, wherein the first circuit unit has a generator comparator element having two inputs and an output, a first input coupled to the generator electrode such that the first input has the electrical potential of the generator electrode,
a second input having a third electrical reference potential, defining the electrical first desired potential,
the generator comparator element is configured to generate an electrical signal at the output such that the electrical potential of the generator electrode is held in the first reference range around the electrical first desired potential,
wherein the third circuit unit has a collector comparator element having two inputs and an output,
a first input is coupled to the collector electrode such that the first input has the electrical potential of the collector electrode,
a second input having a fourth electrical reference potential, defining the electrical second desired potential,
the collector comparator element is configured to generate an electrical signal at the output such that the electrical potential of the collector electrode is held in the first reference range around the electrical second desired potential,
wherein the second circuit unit has a second generator comparator element having two inputs and an output,
the first input is coupled to the first capacitor such that the first input has the electrical potential of the first capacitor,
the second input having a generator reference potential,
the second generator comparator element is configured to generate an electrical signal as an output such that, if the electrical potential of the first capacitor exceeds the generator reference potential, the first capacitor is brought to the first generator reference potential, wherein the fourth circuit unit has a second collector comparator element having two inputs and an output, the first input is coupled to the second capacitor such that the first input has the electrical potential of the second capacitor, the second input having a collector reference potential, the second collector comparator element is configured to generate an electrical signal at an output such that, if the electrical potential of the second capacitor exceeds the collector reference potential, the second capacitor is brought to the collector reference potential, wherein a synchronization element having two inputs and an output includes, a first input coupled to the output of the second generator comparator element, a second input coupled to the output of the second collector comparator element, the synchronization element configured to, in the case of an overlap of the signals at the two inputs, delay one of the signals such that, at one point in time, only the output signal of the second generator comparator element or only the output signal of the second collector comparator element is provided at the output of the synchronization element.

7. The circuit arrangement as claimed in claim 6, wherein the synchronization element has a buffer memory.

* * * * *